(12) United States Patent
Grinstaff et al.

(10) Patent No.: US 12,310,800 B2
(45) Date of Patent: May 27, 2025

(54) INJECTION APPLICATOR FOR TISSUE MARKERS

(71) Applicants: TRUSTEES OF BOSTON UNIVERSITY, Boston, MA (US); BOSTON MEDICAL CENTER CORPORATION, Boston, MA (US)

(72) Inventors: Mark W. Grinstaff, Brookline, MA (US); Boris Nicolas Bloch, Brookline, MA (US); Jonah Kaplan, Newton, MA (US)

(73) Assignees: TRUSTEES OF BOSTON UNIVERSITY, Boston, MA (US); BOSTON MEDICAL CENTER CORPORATION, Boston, MA (US)

( * ) Notice: Subject to any disclaimer, the term of this patent is extended or adjusted under 35 U.S.C. 154(b) by 135 days.

(21) Appl. No.: 16/108,537

(22) Filed: Aug. 22, 2018

(65) Prior Publication Data

US 2018/0353739 A1  Dec. 13, 2018

Related U.S. Application Data

(63) Continuation of application No. 14/646,502, filed as application No. PCT/US2013/071256 on Nov. 21, 2013, now Pat. No. 11,883,246.

(Continued)

(51) Int. Cl.
*A61B 5/00* (2006.01)
*A61B 90/00* (2016.01)
*A61M 31/00* (2006.01)

(52) U.S. Cl.
CPC .......... *A61B 90/39* (2016.02); *A61M 31/005* (2013.01); *A61B 2090/3908* (2016.02);
(Continued)

(58) Field of Classification Search
CPC . A61B 5/064; A61B 90/39; A61B 2090/3904; A61B 2090/3908;
(Continued)

(56) References Cited

U.S. PATENT DOCUMENTS 4,938,901 A * 7/1990 Groitzsch ................ D04H 3/16
604/362
5,300,068 A    4/1994 Rosar
(Continued)

FOREIGN PATENT DOCUMENTS

WO    WO-2006088531 A2 *  8/2006  ....... A61B 17/12145
WO       2006/119645 A1    11/2006
(Continued)

OTHER PUBLICATIONS

Mahony. "An Audit of a Single Institution's Experience of Clip Migration Post Vacuum Assisted Breast Biopsy." European Society of Radiology pp. 1-6 (2002).
(Continued)

*Primary Examiner* — Rajeev P Siripurapu
(74) *Attorney, Agent, or Firm* — NIXON PEABODY LLP; Ronald I. Eisenstein; Ravinderjit S. Braich

(57) ABSTRACT

The inventions provided herein relate to injection applicators, tissue markers and uses thereof, e.g., to mark a target tissue site (e.g., a biopsy site in a breast tissue) or to produce a cell scaffold. The tissue markers described herein are designed to be resistant to fast migration (e.g., immediate migration after implantation through a needle track) and slow migration (e.g., over an extended period of time) upon implantation at a target tissue site (e.g., a biopsy site in a breast tissue), without using an adhesive. Additionally or alternatively, the tissue markers described herein can be readily detectable by at least one imaging modality, e.g., but (Continued)

not limited to magnetic resonance imaging, X-ray imaging, ultrasound imaging, or a combination thereof.

33 Claims, 16 Drawing Sheets

Related U.S. Application Data

(60) Provisional application No. 61/728,971, filed on Nov. 21, 2012.

(52) U.S. Cl.
CPC ............... *A61B 2090/3912* (2016.02); *A61B 2090/3925* (2016.02); *A61B 2090/3954* (2016.02); *A61B 2090/3966* (2016.02); *A61B 2090/3987* (2016.02); *A61B 2090/3991* (2016.02); *A61B 2090/3995* (2016.02)

(58) Field of Classification Search
CPC ...... A61B 2090/3912; A61B 2090/392; A61B 2090/3925; A61B 2090/3937; A61B 2090/3954; A61B 2090/3966
See application file for complete search history.

(56) References Cited

U.S. PATENT DOCUMENTS

| | | | |
|---|---|---|---|
| 5,368,030 A | 11/1994 | Zinreich et al. | |
| 5,857,217 A | 1/1999 | Hsueh | |
| 5,908,493 A | 6/1999 | Krymsky | |
| 6,090,996 A * | 7/2000 | Li | A61L 31/044 606/154 |
| 6,183,497 B1 | 2/2001 | Sing et al. | |
| 6,340,367 B1 | 1/2002 | Stinson | |
| 6,356,782 B1 | 3/2002 | Sirimanne et al. | |
| 6,725,083 B1 | 4/2004 | Burbank et al. | |
| 6,986,763 B2 | 1/2006 | Holmen | |
| 7,329,414 B2 | 2/2008 | Fisher | |
| 7,702,378 B2 | 4/2010 | Bolan | |
| 7,744,852 B2 | 6/2010 | Chernomorsky et al. | |
| 8,064,987 B2 | 11/2011 | Carr | |
| 8,092,513 B2 | 1/2012 | Khosravi et al. | |
| 8,092,779 B2 | 1/2012 | Chernomorsky et al. | |
| 8,280,486 B2 | 10/2012 | Miller et al. | |
| 8,308,814 B2 | 11/2012 | Sengun et al. | |
| 8,491,630 B2 | 7/2013 | Chernomorsky et al. | |
| 8,771,294 B2 | 7/2014 | Sepetka et al. | |
| 9,186,487 B2 | 11/2015 | Dubrul et al. | |
| 9,498,604 B2 | 11/2016 | Dubrul et al. | |
| 9,943,706 B2 | 4/2018 | Corbitt et al. | |
| 2002/0055786 A1 | 5/2002 | Atala | |
| 2002/0151797 A1* | 10/2002 | Montegrande | A61B 90/39 600/458 |
| 2003/0008395 A1 | 1/2003 | Holy | |
| 2003/0097170 A1 | 5/2003 | Friedrich | |
| 2003/0204137 A1 | 10/2003 | Chesbrough | |
| 2004/0054413 A1* | 3/2004 | Higham | A61L 27/52 623/908 |
| 2004/0186377 A1* | 9/2004 | Zhong | A61B 90/39 600/431 |
| 2004/0193044 A1 | 9/2004 | Burbank | |
| 2004/0193066 A1 | 9/2004 | Carlson | |
| 2005/0020899 A1 | 1/2005 | Chernomorsky et al. | |
| 2005/0036946 A1* | 2/2005 | Pathak | A61P 11/06 424/9.4 |
| 2005/0085724 A1 | 4/2005 | Sirimanne | |
| 2005/0119562 A1 | 6/2005 | Jones | |
| 2005/0142163 A1 | 6/2005 | Hunter | |
| 2005/0234336 A1 | 10/2005 | Beckman | |
| 2006/0116712 A1 | 6/2006 | Sepetka et al. | |
| 2006/0129216 A1 | 6/2006 | Hastings | |
| 2006/0173296 A1 | 8/2006 | Miller et al. | |
| 2006/0235094 A1 | 10/2006 | Habibi-Naini | |
| 2006/0247516 A1 | 11/2006 | Hess et al. | |
| 2007/0135711 A1 | 6/2007 | Chernomorsky et al. | |
| 2007/0207186 A1 | 9/2007 | Scanlon et al. | |
| 2007/0231366 A1 | 10/2007 | Sawhney | |
| 2007/0249943 A1* | 10/2007 | Texier-Nogues | A61B 5/0073 600/476 |
| 2007/0292478 A1 | 12/2007 | Youri | |
| 2008/0044900 A1 | 2/2008 | Mooney | |
| 2008/0091120 A1 | 4/2008 | Fisher | |
| 2008/0269603 A1* | 10/2008 | Nicoson | A61B 90/39 600/431 |
| 2009/0131825 A1 | 5/2009 | Burbank | |
| 2009/0221915 A1 | 9/2009 | Voegele | |
| 2009/0297441 A1 | 12/2009 | Canham | |
| 2009/0317335 A1 | 12/2009 | Lin et al. | |
| 2010/0030256 A1 | 2/2010 | Dubrul et al. | |
| 2010/0137679 A1* | 6/2010 | Lashinski | A61B 17/0401 600/37 |
| 2010/0234726 A1 | 9/2010 | Sirimanne | |
| 2010/0249519 A1* | 9/2010 | Park | A61B 17/0218 600/206 |
| 2010/0287887 A1* | 11/2010 | Bolan | A61M 31/002 53/452 |
| 2010/0331668 A1 | 12/2010 | Ranpura | |
| 2012/0078228 A1 | 3/2012 | Michal | |
| 2012/0277859 A1 | 11/2012 | Govil | |
| 2014/0044948 A1 | 2/2014 | Tanaka et al. | |
| 2015/0297316 A1 | 10/2015 | Grinstaff et al. | |
| 2016/0058433 A1 | 3/2016 | Burbank et al. | |
| 2016/0296765 A1 | 10/2016 | Corbitt et al. | |
| 2016/0354178 A1 | 12/2016 | Mayes et al. | |
| 2018/0353738 A1 | 12/2018 | Grinstaff et al. | |
| 2018/0353739 A1 | 12/2018 | Grinstaff et al. | |
| 2019/0192253 A1 | 6/2019 | Yang et al. | |
| 2021/0121263 A1 | 4/2021 | Grinstaff et al. | |

FOREIGN PATENT DOCUMENTS

| | | |
|---|---|---|
| WO | 2008/007048 A1 | 1/2008 |
| WO | 2008/014109 A1 | 1/2008 |
| WO | 2008/076973 A2 | 6/2008 |

OTHER PUBLICATIONS

Rite in the Rain Weatherproof Top-Spiral Notebook, 4"×6", Yellow Cover, Universal Pattern (No. 146). Product sheet [online]. Rite in the Rain, 2006 [retrieved Dec. 17, 2019]. Retrieved from the internet: <URL: https://www.amazon.com/Rite-Rain-Weatherproof-Top-Spiral-Notebook/dp/B000YIGKO8?th=1 >. (Year: 2006).

Toyssa 100 PCS Slap Bracelets Party Favors. Product sheet [online]. Toyssa, 2018 [retrieved Dec. 17, 2019]. Retrieved from the internet: <URL: https://www.amazon.com/Bracelets-Favors-Colorful-Birthday-Classroom/dp/B07D3L9T JG/ref=sr _>. (Year: 2018).

"ATEC Breast Biopsy System for Stereotactic Biopsy", HOLOGIC, retrieved from "https://www.hologic.com/hologic-products/breast-skeletal/atec-breast-biopsy-system-stereotactic-biopsy" on May 14, 2018.

Wolinsky et al., "Local drug delivery strategies for cancer treatment: gels, nanoparticles, polymeric films, rods, and Wafers", J Control Release 159(1) 14-26 (2012).

Wolinsky et al., "Prevention of in vivo lung tumor growth by prolonged local delivery of hydroxycamptothecin using poly(ester-carbonate)-collagen composites", J Control Release 144(3) 280-287 (2010).

Bionumbers (Density and Mass of each organ/tissue; www.bionumbers.hms.harvard.edu/bionumber.aspx?s=n&v=6&id=110244; retrieved Jun. 17, 2023).

Chandrasekharan, Prashant, et al. "Vitamin E (D-alpha-tocopheryl-co-poly (ethylene glycol) 1000 succinate) micelles-superparamagnetic iron oxide nanoparticles for enhanced thermotherapy and MRI." Biomaterials 32.24 (2011); 5663-5672.

* cited by examiner

INJECTION APPLICATOR FOR TISSUE MARKERS

CROSS REFERENCE TO RELATED APPLICATIONS

This application is a continuation of U.S. patent application Ser. No. 14/646,502, filed May 21, 2015, which is a 35 U.S.C. § 371 National Phase Entry Application of international Application No. PCT/US2013/071256 filed Nov. 21, 2013, which designates the U.S., and which claims the benefit under 35 U.S.C. § 119(e) of U.S. Provisional Application No. 61/728,971 filed Nov. 21, 2012, the contents of each of which are incorporated herein by reference in their entirety.

TECHNICAL FIELD OF THE DISCLOSURE

The inventions described herein generally relate to tissue markers and uses thereof. In some embodiments, the tissue markers described herein can be used to mark a target tissue site, e.g., a biopsy site in various tissues including, but are not limited to, a breast, colon, rectal, liver, ovarian, prostate, and/or lung tissue. In some embodiments, the tissue markers described herein can be used as cell scaffolds.

BACKGROUND

Many cancers such as breast and prostate cancers are typically diagnosed using minimally invasive biopsies of the suspicious tissue with a tissue-coring needle. During the biopsy, or immediately thereafter, a tissue marker is placed in the tissue void space, for example, for future reference/biopsy or examination, for surgical removal of tissue surrounding the biopsy area after confirmatory diagnosis, for avoiding sampling the same area in future biopsies, and/or for use as a fiducial marker in treatment, e.g., radiation treatment planning Imaging of a tissue with or without tissue markers can be performed using conventional imaging modalities. Examples of conventional imaging modalities include ionizing radiation imaging (e.g., x-ray imaging, computed tomography (CT), or mammography), magnetic imaging (e.g., magnetic resonance imaging (MRI)), and ultrasound imaging.

Conventional tissue markers typically consist of one of more solid objects, such as a piece of metallic wire, ceramic beads, etc., which are implanted either by themselves or within a gelatinous matrix to increase visibility to imaging such as ultrasound, MRI, or x-ray imaging.

The conventional markers have been shown to have a few significant problems associated with their use. For example, titanium-based clips or tissue markers typically produce small MRI and ultrasound signals and may distort the surrounding tissue, depending on the scan/sequence used. Other clips or tissue markers may not be seen on all three main imaging techniques used (MRI, x-ray, ultrasound). Some clips or tissue markers are bio-resorbable (e.g., collage-based plugs) and thus lose ultrasound visibility after about 6 months. In addition, the surface and shape of these clips or tissue markers are generally smooth and narrow, respectively; therefore, the clips or tissue markers can be drawn back immediately into a biopsy needle when the needle is withdrawn from the tissue, or dense metal markers can migrate through the less dense tissue over time, resulting in poor image registration and inaccurate biopsy site location in subsequent examinations and imaging. Accordingly, there is a need to develop tissue markers that can provide precise lesion or biopsy location over an extended period of time, e.g., for targeted treatments or follow-up monitoring. Further, there is a need for tissue markers that can be readily visible on MRI, ultrasound, and/or mammography so that a lesion can be detected in a minimally-invasive manner.

SUMMARY

Existing tissue markers (e.g., biopsy markers) generally have issues with securing the tissue markers in place at a target site after implantation. For example, a typical rigid, smooth tissue marker in its single defined form (e.g., a cylinder) can migrate through a implantation needle track due to the negative pressure caused by the simultaneous withdrawal of the delivery needle (fast migration), and/or it can migrate slowly over time through the void space and needle track due to normal physiological movements (slow migration), thus resulting in poor image registration and inaccurate marker site location in subsequent examinations and imaging.

To this end, the inventors have developed, in some embodiments, flexible polymeric tissue markers and methods of using the same to overcome the aforementioned challenges associated with the existing tissue markers and to mark a tissue without using an adhesive. In some embodiments, a tissue marker described herein can comprise a flexible polymeric film with at least the density and electrostatic pressure substantially the same as (i.e., similar to) the target tissue, thus preventing the tissue marker, without using an adhesive, from slow migration over time. Further, the flexible polymeric film can be adapted to be visible by at least one or more imaging modalities. Additionally, the flexible polymeric film can adopt different configurations or forms as its surrounding volume or degree of confinement varies. For example, a flexible polymeric film can adopt a compact configuration or form, e.g., a rolled-up hollow cylinder, when it is loaded into a needle cannula. Upon ejection at a target tissue site, the polymeric film can flexibly adopt an expanded configuration or form that is sufficient to "lock" the tissue marker in place without using an adhesive, thus preventing migration of the tissue marker away from the implantation site. In one embodiment, a rolled-up flexible polymeric film originally loaded into a needle cannula can start to unroll, upon deployment, to either restore its original planar shape or form a partially unrolled cylinder having a larger diameter than the cross-section of the needle track.

Furthermore, the tissue marker can comprise penetrating pores that can allow cellular infiltration. Thus, tissue can grow around or into an implanted tissue marker at the edges or through the pores, providing further anchorage of the tissue marker to the target tissue site, and/or producing a scaffold of cells. Accordingly, embodiments of various aspects described herein relate to tissue markers and methods of using the same. In some embodiments, the tissue markers can be used to mark a tissue. Additionally or alternatively, the tissue markers can be used as a scaffolding material and thus form a scaffold comprising a plurality of cells.

In one aspect, methods, e.g., of marking a target tissue site, are described herein. The method comprises implanting into tissue at a target tissue site a tissue marker having a flexible polymer matrix arranged in a compact configuration, wherein the flexible polymer matrix has a density and an electrostatic pressure substantially the same as the target tissue, and wherein upon the implantation at the target tissue site, the flexible polymer matrix transforms from the compact configuration to an expanded configuration while maintaining the density, and does not migrate for an extended period of time, wherein the target tissue is not an eye tissue. In some embodiments, the target tissue is not a lens capsule.

The tissue marker described herein can be implanted into a tissue in need thereof, excluding an eye or ocular tissue, e.g., a lens capsule. In some embodiments, the tissue amenable to implantation of the tissue marker therein can be a soft tissue. Non-limiting examples of a soft tissue include a breast, colon, rectal, liver, ovarian, prostate, or lung tissue. In some embodiments, the tissue marker described herein can be implanted into a breast tissue.

In some embodiments, the tissue marker can be implanted into tissue at a target tissue site without the use of an adhesive, e.g., a glue or sealant that is generally used to attach or seal two surfaces (e.g., a tissue surface and the tissue marker surface) together. In some embodiments, the implanted tissue marker can be secured at a target tissue site without the use of an adhesive.

The target tissue site at which the tissue marker is to be implanted can be any site in a tissue to be marked. For example, the target tissue site can be at, or in close proximity to, a void space or cavity, a lesion, a wound, a biopsy site, a diseased tissue area, a tissue area to be diagnosed, or any combinations thereof. In some embodiments, the target tissue site can be at, or in close proximity to, the site of a first biopsy. In one embodiment, the target tissue site is at the site of a first biopsy. The site of the first biopsy can be a void space created after the first biopsy is performed, or alternatively be a site in close proximity or adjacent to a tissue to be biopsied. Thus, in some embodiments, the methods described herein can be used to mark a first biopsy site or area in a tissue. In these embodiments, the methods can further comprising performing a first biopsy prior to implanting one or more tissue markers into the first biopsy area. In one embodiment, the methods described herein can be used to mark a biopsy site or area in a breast tissue.

Unlike existing and conventional tissue markers, the tissue markers described herein, upon implantation, do not migrate away from the target tissue site (or implantation site) over an extended period of time, thus providing a more accurate location of the implantation site for future reference, biopsy, examination and/or treatment. Accordingly, the method described herein, in some embodiments, can further comprise determining the location of the implanted tissue marker in the tissue at a first time point. In some embodiments, the method can further comprise determining the location of the implanted tissue marker in the tissue at a second time point, wherein the second time point is subsequent to the first time point.

By more accurately or reliably identifying the location of the biopsy site using the tissue markers described herein, repeated sampling of the same biopsy area can be minimized or avoided. Thus, in some embodiments, the method can further comprise performing a second biopsy at a site different from the target tissue site marked by the tissue marker. In some embodiments, the second biopsy can be performed at a site distant from the target tissue site marked by the tissue marker. In some embodiments, the second biopsy can be performed in close proximity to, but not at, the target tissue site marked by the tissue marker.

Marking a target tissue site with one or more tissue markers described herein can also facilitate treating and/or monitoring or examining a condition of the same tissue at, or in close proximity to, the target tissue site marked by the tissue marker(s). In these embodiments, the method can further comprise examining the tissue at, or in close proximity to, the same target tissue site at a second time, wherein said second time point is subsequent to the first time point. In some embodiments, the method can further comprise removing or treating tissue surrounding the same target tissue site at a time point that is after the tissue marker is implanted.

In some embodiments, the flexible polymer matrix of the tissue marker described herein can further comprise macropores. In these embodiments, at least one of the cells in the tissue surrounding the implanted tissue marker can infiltrate into the macropores. In such embodiments, the method can further comprise growing a plurality of cells into the macropores. This can provide further anchorage of the tissue marker at the implantation site.

As cells can infiltrate and grow in the macropores of tissue markers upon implantation, the tissue markers can also be used as a scaffold. For example, the tissue markers described herein can be used to collect cells from tissues surrounding the implantation site and/or to facilitate tissue integration and/or regeneration at the target tissue site. Accordingly, in another aspect, methods, e.g., of producing a scaffold comprising a plurality of cells, are provided herein. The method can comprise (a) implanting into tissue at a target tissue site a tissue marker having a flexible polymer matrix arranged in a compact configuration, wherein the flexible polymer matrix comprises macropores and has a density substantially the same as the tissue, and wherein upon the implantation at the target tissue site, the flexible polymer matrix transforms from the compact configuration to an expanded configuration while maintaining the density, and (b) growing a plurality of cells into the macropores. In some embodiments, the tissue marker is not implanted in an eye tissue. In some embodiments, the tissue marker is implanted in a soft tissue, including, e.g., but are not limited to, a breast, colon, rectal, liver, ovarian, prostate, or lung tissue.

In some embodiments, the tissue marker can be implanted without the use of an adhesive, e.g., a glue or sealant that attaches or seals two surfaces (e.g., a tissue surface and the tissue marker surface) together. In some embodiments, the tissue marker can be secured at the target tissue site for a period of time without the use of an adhesive.

In some embodiments, the tissue marker can have an electrostatic pressure substantially the same as the tissue to be implanted.

In some embodiments of this aspect and other aspects described herein, the macropores present in the flexible polymer matrix of the tissue markers can be adapted to provide sites for cell infiltration, growth and proliferation, which can provide additional anchorage of the tissue marker at the implantation site and/or form a cell scaffold. In some embodiments, the macropores can form channels between two opposing surfaces of the flexible polymer matrix. In some embodiments, the macropores can penetrate through both opposing surfaces of the flexible polymer matrix.

The channels of the macropores can have a dimension (e.g., diameter) sufficient for at least one cell to reside, e.g., depending on number of cells desired to be grown therein. In some embodiments, the macropores can have a dimension (e.g., diameter) of about 0.05 mm to about 2 mm. In some embodiments, the macropores can have a dimension (e.g., diameter) of about 0.2 mm to about 2 mm. In some embodiments, the macropores can have a dimension (e.g., diameter) of about 1 mm to about 2 mm.

In some embodiments of this aspect and other aspects described herein, the tissue markers can be readily detected in a minimally-invasive manner. For example, in some embodiments, the flexible polymer matrix of the tissue markers described herein can be adapted to be detectable by at least one imaging modality. In some embodiments, the flexible polymer matrix can be further adapted to be detectable by at least two imaging modalities. In some embodiments, the flexible polymer matrix can be further adapted to be detectable by least three imaging modalities. Examples of imaging modalities include, but are not limited to, magnetic resonance imaging, mammography, X-ray-based imaging, ultrasound imaging, fluorescence imaging, computed tomography imaging and any combinations thereof. In one embodiment, the flexible polymer matrix can be further adapted to be detectable by at least magnetic resonance imaging, X-ray-based imaging, and ultrasound imaging.

The methods of various aspects described herein can generally be applicable to mark any tissue in a subject or to make a scaffold comprise a population of any tissue cells, wherein the tissue is not an ocular or eye tissue. In some embodiments, the target tissue amenable to the methods described herein can be a soft tissue, e.g., adipose tissue, breast tissue, colon tissue, rectal tissue, liver tissue, ovarian tissue, prostate tissue, or lung tissue. In some embodiments, the target tissue amenable to the methods described herein is breast tissue.

In accordance with some embodiments of various aspects described herein, the tissue markers do not migrate for an extended period of time. For example, in some embodiments, the tissue marker does not migrate away from the target tissue site by a distance of more than 10 mm (including not more than 5 mm or less) over an extended period of time. The extended period of time can be at least about 1 month, at least about 2 months, at least about 3 months, at least about 6 months, at least about 1 year or at least about 2 years. In one embodiment, the tissue marker does not migrate away from the target tissue site by a distance of more than 5 mm (including not more than 1 mm) over a period of at least about 1 month. In some embodiments, the tissue marker does not migrate away from the target tissue site by a distance of more than 1 mm over a period of at least about 2 years, not more than 5 mm over a period of at least about 2 years, or not more than 10 mm over at least about 2 years.

The tissue marker(s) described herein can be implanted into tissue at a target tissue site by any methods known in the art. For example, the tissue marker(s) described herein can be implanted into tissue at a target tissue site by injection, catheterization, and/or insertion through a cannula. In some embodiments, the tissue marker can be implanted into tissue at a tissue target site through an injection applicator. By way of example only, an injection applicator can comprise a needle, a cannula, a catheter, or any combinations thereof.

In accordance with various aspects described herein, the compact configuration of a tissue marker can be a geometric configuration of the flexible polymer matrix resulted from a compaction force or compressive force. In some embodiments, the compact configuration of a tissue marker can be resulted from confinement of the tissue marker inside an injection applicator. In such embodiments, the compact configuration of a tissue marker can adopt the inner cross-sectional shape and/or size of an injection applicator. For example, if the injection applicator includes a needle, of which the lumen has a cylindrical cross-section, the flexible polymer matrix of the tissue marker can adopt a cylindrical configuration to fit inside lumen of the needle.

Upon implantation at a target tissue site, the flexible polymer matrix of the tissue marker is released from the compact configuration and adopts an expanded configuration while maintaining its density. The flexible polymer matrix in the expanded configuration usually conforms to surrounding space at the implantation site (the target tissue site), thereby preventing the tissue marker from being pulled back into an injection applicator upon its withdrawal from the target tissue site (fast migration). In some embodiments, the flexible polymer matrix in an expanded configuration can maintain a similar geometric configuration as in a compact configuration, but in a more expanded form. For example, the flexible polymer matrix can maintain the geometric configuration of the compact configuration, but have at least one of the dimensions larger than those in the compact configuration. By way of example only, if the flexible polymer matrix is originally a square film and is confined as a cylinder in a needle cannula, the expanded configuration of the tissue marker after implantation can be, for example, a straight or bent square film (if the surrounding space allows), a partially unrolled cylinder with dimensions larger than the needle track, or an expanded form of a hollow cylinder.

While the flexible polymer matrix can be in any format (e.g., but not limited to, a film, or a collection of fibers such as a woven or non-woven mat or mesh), in some embodiments, the flexible polymer matrix can form a film. In alternative embodiments, the flexible polymer matrix can form a mesh. In some embodiments, the flexible polymer matrix can form a mat. The flexible polymer matrix, e.g., in a form of a film, mat or mesh, can have a thickness that provides sufficient flexibility in response to the changes in surrounding space and degree of confinement. In some embodiments, the flexible polymer matrix, e.g., in a form of a film, can have a thickness of about 0.05 mm to about 4 mm. The dimension or width of the flexible polymer matrix, e.g., a film or mesh, can vary, for example, with different applications, size of target tissue site or void, and/or methods of implantation. In some embodiments, the flexible polymer matrix (e.g., in a form of a film) can have a dimension or width of about 0.2 cm to about 1.5 cm.

The flexible polymer matrix can be adapted to be resistant to degradation upon the implantation at the target tissue site, or it can be adapted to be biodegradable. In some embodiments, the flexible polymer matrix can be tuned to degrade after implantation for a period of time. Non-limiting examples of degradation-resistant polymeric materials suitable for use in the flexible polymer matrix can include polyethylene, polypropylene, polytetrafluoroethylene, polyurethanes, polystyrene, polypropylene glycol, any art-recognized degradation-resistant polymers, or any combinations thereof. Examples of biodegradable polymeric materials suitable for use in the flexible polymer matrix can include, but are not limited to, polyester, polyamide, polycarbonate, polyhydroxyacids (e.g., but not limited to, polylactic acid and polyglycolic acid), polycaprolactone, and any combinations thereof.

In some embodiments, the flexible polymer matrix can comprise a viscoelastic (including, but not limited to "shape-memory" polymer) and/or elastic polymer.

The flexible polymer matrix can comprise at least one or more polymeric materials, including, e.g., at least two, at least three, at least four or more polymeric materials. Non-limiting examples of polymeric materials for use in fabrication of the flexible polymer matrix include degradation resistant polymers, biodegradable polymers, viscoelastic polymers, elastic polymers, and any combinations thereof.

In some embodiments, the flexible polymer matrix can comprise an agent or material that enhances the flexibility or elasticity of the selected polymer material(s) and/or the transformation between the compact configuration and the expanded configuration. In one embodiment, the agent that enhances the flexibility or elasticity of the selected polymer material(s) and/or the transformation between the compact configuration and the expanded configuration includes at least one shape-memory alloy material and/or at least one elastic material. Exemplary shape-memory alloy material and/or elastic material includes, but is not limited to, copper-aluminum-nickel alloys, nickel-titanium (NiTi) alloys or nitinol, alloys comprising at least two or more of zinc, copper, gold and iron, and any combinations thereof. The shape-memory alloy material and/or elastic material can be provided in any shape, e.g., but not limited to, straight or curved wire, ribbon, coil, an intertwining structure, or any combinations thereof. In one embodiment, the flexible polymer matrix can comprise at least one or more nitinol wires.

In some embodiments, the flexible polymer matrix can be adapted to suit for detection by desired imaging modality/modalities. For example, in some embodiments, at least one material forming the flexible polymer matrix can produce a signal detectable by at least one or more imaging modalities. Where at least one of the imaging modalities involves ultrasound imaging, the flexible polymer matrix can comprise polyethylene, polypropylene, polytetrafluoroethylene, polyurethanes, polyester, polyamide (e.g., nylon-6, nylon-6,6, nylon-12), polycarbonate, or any combinations thereof.

In some embodiments, the flexible polymer matrix can comprise one or more contrast agents detectable by the at least one or more imaging modalities. The contrast agent(s) can be coated on the flexible polymer matrix, and/or mixed, embedded, dispersed, or suspended in the flexible polymer matrix. The contrast agent(s) can be independently selected to produce a change in signal intensity under at least one or more imaging modalities, and/or to provide visibility under at least one or more imaging modalities. For example, the contrast agent(s) can be independently selected to produce a decrease in signal intensity under MRI, and/or it can be selected to provide visibility under x-ray and/or ultrasound imaging.

In some embodiments, the flexible polymer matrix can comprise at least one contrast agent detectable by at least magnetic resonance imaging (MRI). Examples of MRI-detectable contrast agent(s) include, without limitations, metal oxide particles (e.g., but not limited to, iron oxide particles), metal materials, amorphous materials, crystalline materials, and any combinations thereof. Additionally or alternatively, the flexible polymer matrix can comprise at least one contrast agent detectable by at least X-ray imaging. Exemplary X-ray-detectable contrast agent(s) include, but not limited to, a radiopaque material (e.g., loxaglate or iodine (HEXABRIX® or CYSTO CONRAYTMII), bromine, salts (e.g., an iodinated salt, barium salts (e.g., barium sulfate), bismuth salts (e.g., bismuth oxychloride), or any combinations thereof), metal or alloy materials (e.g., nitinol, titanium, tantalum, tungsten, or any combinations thereof), metal oxide particles, and any combinations thereof.

In some embodiments, the contrast agent(s) selected to be included in the flexible polymer matrix can be detectable by at least two or more imaging modalities. For example, metal or alloy materials (e.g., nitinol) can be detectable by at least both MRI and X-ray imaging.

In some embodiments, the contrast agent(s) can be formed by integrating at least two contrast agents to form an integral entity. For example, in some embodiments, the contrast agent can comprise an iron oxide particle coated with a different contrast agent, e.g., an iodinated salt.

In some embodiments, the flexible polymer matrix can further comprise an imaging signal enhancer. An exemplary imaging signal enhancer includes a plurality of gas-filled microbubbles. The gas-filled microbubbles can be detected by ultrasound imaging. Examples of a gas used to form microbubbles include, but are not limited to, air, nitrogen, oxygen, carbon dioxide, argon, helium, perfluorocarbon gases, and any combinations thereof.

In some embodiments, the tissue markers described herein can be used to deliver at least one active agent to the target tissue site and/or surrounding tissue. In these embodiments, the flexible polymer matrix to be implanted at the target tissue site can comprise at least one active agent. In some embodiments, the active agent(s) can be added into or coated on the flexible polymer matrix during fabrication of the tissue marker or prior to the implantation. Additionally or alternatively, the active agent can be separately delivered to the target tissue site (e.g., by injection) prior to, concurrently with, or after the implantation of the tissue marker. Examples of an active agent include, but are not limited to a therapeutic agent, a radioisotope for radiation therapy, a chemotherapeutic, an antimicrobial agent (e.g., antibiotics or an antiseptic agent), an anesthetic, a cell growth factor, a peptide, a steroid, a carbohydrate, a lipid, a non-steroidal anti-inflammatory drug (NSAID), a peptidomimetic, an antibody or a portion thereof, an antibody-like molecule, nucleic acid, and any combinations thereof. In one embodiment, the active agent to be delivered to the target tissue site and/or surrounding tissue can comprise an antimicrobial agent (e.g., antibiotics or an antiseptic agent).

Additional objects, advantages, and features will become apparent from the following description and the claims that follow, considered in conjunction with the accompanying drawings.

BRIEF DESCRIPTION OF THE DRAWINGS

FIG. 2A is a mammogram of a chicken breast injected with a tissue marker containing HEXABRIX® as a radiocontrast agent, as depicted by a bright spot. FIG. 2B is a mammogram of a chicken breast injected with a tissue marker containing a titanium wire as a radio-contrast agent, as depicted by a bright rod shape. FIG. 2C is a mammogram of a chicken breast injected with tissue markers either containing HEXABRIX® (top portion of the image) or potassium iodide (bottom portion of the image), as a radiocontrast agent. FIG. 2D is a mammogram of a chicken breast injected with tissue markers containing various nitinol wire lengths (top to bottom: no wire, ~0.25 cm, ~0.5 cm, ~0.75 cm, ~1.0 cm, ~1.25 cm, ~1.5 cm of nitinol wire).

FIG. 4A is a magnetic resonance image of a chicken breast injected with a tissue marker comprising superparamagnetic iron oxide particles. FIG. 4B is a magnetic resonance image of 1% agar gel phantom loaded with tissue markers containing various iron oxide nanoparticles (top center (H) through clockwise orientation: 0.5 mg, 0.25 mg, 0.125 mg, 0.0625 mg, 0.01 mg and 0 mg particles). FIG. 4C is a magnetic resonance image of a chicken breast injected with a tissue marker comprising superparamagnetic iron oxide particles.

FIG. 5A is a schematic diagram showing a melt process for fabrication of a tissue marker described herein. FIG. 5B is a schematic diagram showing a solvent casting process for fabrication of a tissue marker described herein.

FIG. 6A shows the tissue marker loaded into the introducer. FIG. 6B shows the tissue marker beginning to unroll after partial deployment from the introducer. FIG. 6C shows the tissue marker immediately after deployment, and further shows the partial unrolling upon deployment. In this embodiment, the term "unrolling" is defined herein as a change from a cylindrical shape, as existing in confinement within the introducer, to a larger-diameter shape after being released from confinement in the introducer.

FIG. 9A is an image of an example tissue marker fabricated using a melt processing sealing method as described in Example 3. In this embodiment, the tissue marker contains iron oxide nanoparticles and a Nitinol wire. FIG. 9B is an image of an example tissue marker fabricated using a solvent casting and melt sealing method as described in Example 4. In this embodiment, the tissue marker contains iron oxide nanoparticles and a Nitinol wire.

FIG. 11A shows the tissue marker according to one embodiment (right side) and a commercially available biopsy marker (left side) partially deployed from respective introducer needles. FIG. 11B shows the inventive tissue marker (enclosed within the rectangle) and the commercially available biopsy marker immediately after deployment. FIG. 11C shows the inventive tissue marker with a Nitinol wire having a length dimension of about 4 mm, as compared to the introducer needle with a diameter dimension of about 3 mm, indicating at least partial unrolling after deployment. FIG. 11D shows the inventive tissue marker and the commercially available biopsy marker remaining at their deployment site after removing their introducer needles.

FIG. 14A is a set of MRI images of ~1% agar gel phantom incorporated with tissue markers comprising various amounts of iron oxide nanoparticles. The MRI images were captured using BiLateral Imaging in Sagittal view with Sense (BLISS) (upper panel) and Turbo Spin Echo (TSE) (lower panel) methods. FIG. 14B is a plot of quantified size/volume artifacts as a function of the mass of iron oxide nanoparticles.

FIG. 15A shows tissue growth around the tissue marker after 1 week of implantation. Left image is 4× magnification; right image is 20× magnification. FIG. 15B shows tissue growth around the tissue marker after 4 weeks of implantation. Left image is 4× magnification; right image is 20× magnification.

DETAILED DESCRIPTION OF THE INVENTION

Figure 1:
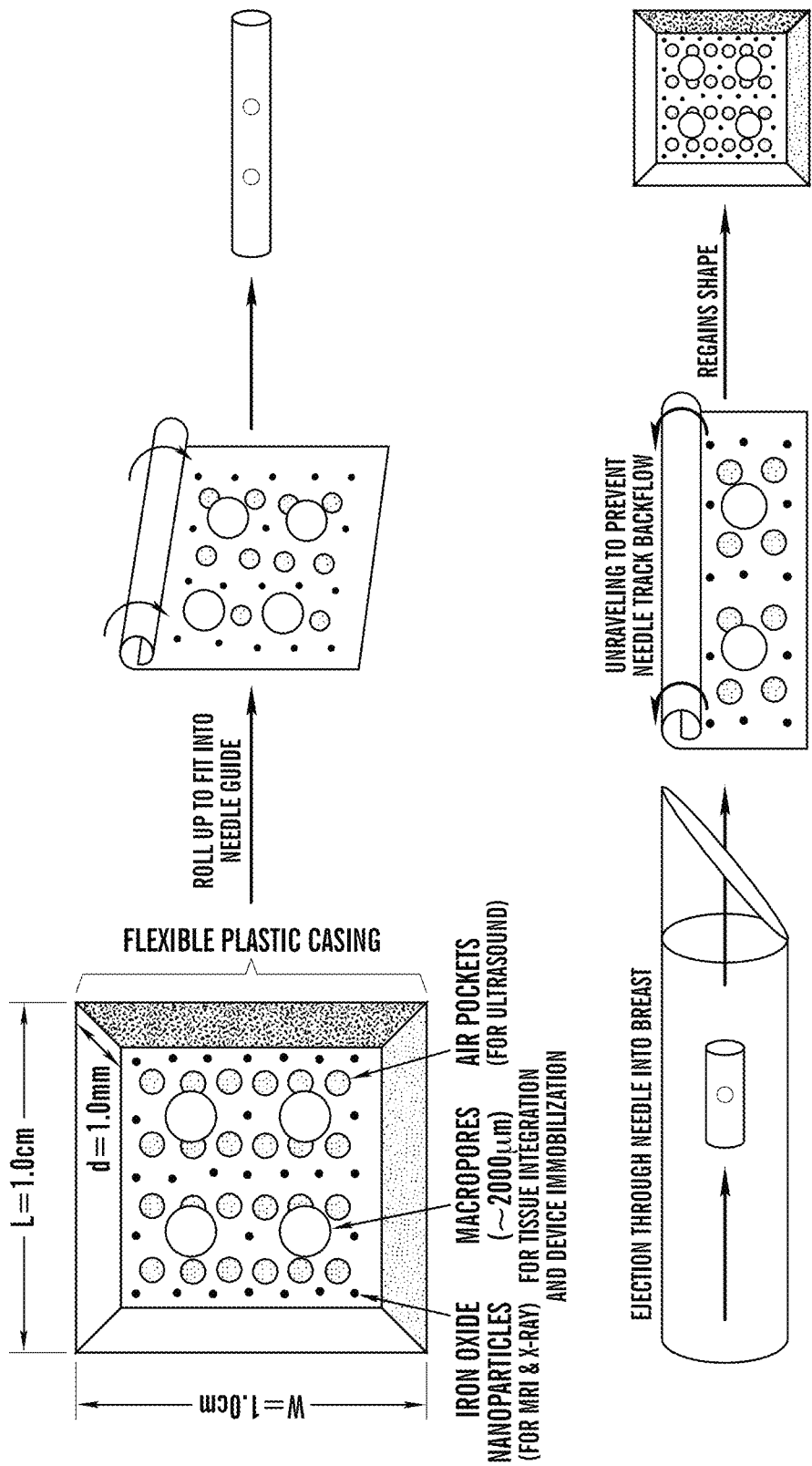
FIG. 1 is a diagrammatic illustration of one embodiment of a tissue marker described herein and an exemplary implantation mechanism. While a shape-memory alloy or elastic material (e.g., but not limited to, a nitinol wire) is not shown in this embodiment, in some embodiments, the tissue marker can comprise a shape-memory alloy or elastic material (e.g., but not limited to, a nitinol wire) in the flexible polymer matrix.

Existing tissue markers (e.g., biopsy markers) can migrate through the needle track either due to the negative pressure caused by the simultaneous withdrawal of the delivery/deployment needle and/or biopsy needle (fast migration), or due to incomplete disengagement of the tissue marker from the deployment device, which in turn results in the tissue marker being pulled back during removal of the deployment needle, and/or they can migrate slowly over time through low density tissue (e.g., fatty tissue) due to normal physiological movements (slow migration), thus resulting in poor image registration and inaccurate marker site location in subsequent examinations and imaging, inaccurate treatment planning. Accordingly, there is a need to develop tissue markers that resist both fast and slow migration in order to provide precise marking location in a tissue over an extended period of time, e.g., for targeted treatments or follow-up monitoring.

Embodiments of various aspects described herein stem in part from development of a novel tissue marker comprising a flexible polymeric matrix that is adaptable to more than one configuration, e.g., depending on its degree of confinement, and has a density substantially the same as the tissue. For example, the flexible polymeric matrix can initially adopt a compact configuration when it is loaded within an injection applicator; but then take an expanded configuration when it is inserted at a target tissue site upon implantation. Thus, the tissue markers described herein can be implanted at a target tissue site with a minimally-invasive procedure, and can also "lock" in place upon implantation without using an adhesive, thus preventing fast migration of the tissue marker caused by withdrawal of the delivery needle and/or biopsy needle. By way of example only, when confined within the needle cannula, the flexible polymeric film can be manipulated, e.g., by rolling up, to form a hollow cylinder, but upon ejection into a target site, the elasticity of the polymeric film can cause, e.g., spring-like unrolling, and thus change its previous geometric configuration accordingly to form a partially-unrolled hollow cylinder having a larger diameter than the needle cannula, or to restore its planar configuration. This spring-like unrolling can be further enhanced by the presence of a shape-memory alloy or an elastic material (e.g., but not limited to, a thin elastic nitinol wire) in the flexible polymeric matrix. Further, the flexible polymeric matrix has a density substantially the same as the target tissue, thus preventing the tissue marker, without using an adhesive, from slow migration over time. In some embodiments, the flexible polymeric matrix can also have an electrostatic pressure substantially the same as the target tissue, thereby preventing the tissue marker, without using an adhesive, from fast migration and/or slow migration over time. Additionally, the flexible polymeric film can further comprise penetrating macropores that can allow cellular infiltration. Thus, cells and/or tissue can grow around or into the edges and/or macropores of the tissue marker, providing further anchorage of the tissue marker to the target tissue site, and/or producing a scaffold of cells. Accordingly, embodiments of various aspects described herein relate to tissue markers and methods of using the same. In some embodiments, the tissue markers described herein can be used to mark a tissue. In some embodiments, the tissue markers described herein can be used as a scaffolding material to form a scaffold comprising a population of cells and/or a tissue.

Methods of Using One or More Embodiments of the Tissue Markers Described Herein

In one aspect, a method, e.g., of marking a target tissue site is described herein. The method comprises implanting into a tissue at a target tissue site a tissue marker having a flexible polymer matrix arranged in a compact configuration, wherein the flexible polymer matrix has a density and an electrostatic pressure substantially the same as the target tissue, and wherein upon the implantation into the target tissue site, the flexible polymer matrix transforms from the compact configuration to an expanded configuration while maintaining the density, and does not migrate for an extended period of time. Preferably the tissue is not an eye tissue. In some embodiments, the tissue is not a lens capsule.

In some embodiments, the flexible polymer matrix can comprise an agent or material that enhances the flexibility or elasticity of the selected polymer material(s) and/or the transformation between the compact configuration and the expanded configuration. In one embodiment, the agent that enhances the flexibility or elasticity of the selected polymer material(s) and/or the transformation between the compact configuration and the expanded configuration includes at least one shape-memory alloy material and/or at least one elastic material. Exemplary shape-memory alloy material and/or elastic material includes, but is not limited to, copper-aluminum-nickel alloys, nickel-titanium (NiTi) alloys or nitinol, alloys comprising at least two or more of zinc, copper, gold and iron, and any combinations thereof. The shape-memory alloy material and/or elastic material can be provided in any shape, e.g., but not limited to, straight or curved wire, ribbon, coil, an intertwining structure, bullet shape, hour-glass shape, cross shape, or any combinations thereof. In one embodiment, the flexible polymer matrix can comprise at least one or more nitinol wires.

In various aspects described herein, the tissue markers can be implanted into a tissue in need thereof, excluding an eye or ocular tissue, and a lens capsule. In some embodiments, the tissue amenable to implantation of the tissue marker(s) described herein can be a soft tissue. An exemplary tissue amenable to the method described herein includes, but not limited to, a breast, colon, rectal, liver, ovarian, prostate, or lung tissue. In some embodiments, the tissue markers described herein can be implanted into a breast tissue.

In some embodiments of this aspect and other aspects described herein, the tissue marker is implanted into a tissue at a target tissue site without the use of an adhesive. In some embodiments, the implanted tissue marker is secured at a target tissue site without the use of an adhesive. In some embodiments, the tissue marker does not migrate upon implantation in the absence of an adhesive. As used herein, the term "adhesive" refers to a glue, a sealant, or any sticky material that is generally used to attach, bond or seal two surfaces together. In the context of the inventions described herein, an adhesive refers to a glue, a sealant, or any sticky material that is generally biocompatible and is generally used to attach, bond, or adhere an implantable component or device to surrounding tissue. Examples of an adhesive can include, but are not limited to, a polyurethane compound, a cyanoacrylate, an epoxide, a polyacrylic compound, polyhydroxymethacrylate, a fibrin glue or sealant (e.g., TISSEAL™), collagen adhesive, or any combinations thereof.

In various aspects described herein, the tissue marker can be implanted into a tissue at a target tissue site by any methods known in the art. Methods for implanting one or more tissue markers described herein include, but are not limited to, direct insertion (e.g., without an injection applicator), injection, catheterization, and/or insertion through a cannula. In some embodiments, the tissue marker can be implanted into a tissue at a target tissue site through use of an injection applicator. Exemplary injection applicators include, but are not limited to, a needle, a cannula, a catheter, and any combinations thereof. In one embodiment, the tissue marker can be implanted into the tissue at the target tissue site using a biopsy device.

The term "expanded configuration" as used herein refers to a post-implantation geometric configuration attained by the flexible polymeric matrix conforming or adjusting to size and shape of the space at or surrounding the target tissue site (e.g., but not limited to, a void resulted from a biopsy), while maintaining the density of the flexible polymer matrix. In some embodiments, the expanded configuration of the tissue markers can have at least one dimension comparable to (e.g., within 15% or less, within 10% or less, within 5% or less, or within 1% or less) a dimension of the target tissue site or area such that the tissue marker can stay or anchor at the target tissue site without migration over time. In some embodiments, the expanded configuration of the tissue markers can have at least one dimension larger than (e.g., by at least about 1%, at least about 2%, at least about 5%, at least about 10% or more) a dimension of the target tissue site or area such that the tissue marker presses against surrounding tissue of the implantation site and thus does not migrate over time. The transformation of the flexible polymer matrix from the compact configuration to the expanded configuration does not cause any substantial change in molecular structure of the matrix material or the inherent material density of the flexible polymer matrix. In some embodiments where a shape-memory material or alloy material and/or elastic material is included in the flexible polymeric matrix, the shape-memory material or alloy material and/or elastic material can transform from a compact configuration to an expanded configuration. The transformation of the shape-memory material or alloy material and/or elastic material can enhance the transformation of the flexible polymeric matrix between the compact configuration and the expanded configuration. In one embodiment, a nitinol wire can be included as a shape-memory alloy material or an elastic material in the flexible polymeric matrix.

In some embodiments, the transformation of the tissue markers from a compact configuration to an expanded configuration is not induced by introducing air or other gases into the tissue markers when they are in a compact configuration. In some embodiments, the transformation of the tissue markers from a compact configuration to an expanded configuration is not caused by swelling of the matrix material upon implantation. Rather, without wishing to be bound by theory, the tissue markers in a compact configuration gains elastic potential energy as they are physically manipulated (e.g., rolling and/or folding) to reduce at least one of its dimension for fitting into a smaller space, e.g., a cannula for injection. Upon implantation into a tissue, at least a portion of the stored elastic potential energy is released, causing the flexible polymer matrix to unroll, unfold, or unravel and thus adopt a larger shape or geometric configuration. For polymers having a more viscous (rather than elastic) property, addition of shape-memory alloy material(s) and/or elastic material(s), e.g., but not limited to, a thin elastic nitinol wire, can provide additional elastic contributions to the unrolling, unfolding, and/or unraveling of the tissue markers described herein.

As used herein, the phrase "maintaining the density" refers to no substantial changes in the molecular structure of the material and/or inherent or material density of the flexible polymer matrix. In some embodiments, the phrase "maintaining the density" refers to the density of the flexible polymer matrix in a compact configuration being the same as or identical to the density of the flexible polymer matrix in an expanded configuration. As used herein, the term "density" refers to volumetric mass density of a material, which is determined by the material mass divided by material volume. Unlike some existing gel-based tissue markers that can swell in material volume (e.g., due to hydration) to fill the space of the target tissue site, which can in turn affect their material density, the tissue markers described herein can transform their geometric configuration to fill the space of the target tissue site and/or to anchor at the target tissue site without changing the molecular structure of the material or inherent density. By way of example only, transformation from a 3-D configuration (e.g., a roll-up hollow cylinder) to a 2-D configuration (e.g., a planar film) or a 3-D configuration in a shape having a different dimension (e.g., a partially unrolled cylinder) does not change the molecular structure of the material or inherent density of the flexible polymer matrix.

The term "compact configuration" as used herein refers to a pre-implantation geometric configuration with at least one dimension of the flexible polymer matrix smaller than the dimensions of the flexible polymer matrix in an expanded configuration described herein. In some embodiments, the size and/or shape of the compact configuration can be adjusted to minimize the invasiveness of the implantation procedure, and/or based on the lumen space of the selected injection applicator, e.g., but not limited to, a needle, a cannula, a catheter, or any combinations thereof. In some embodiments, the compact configuration of a tissue marker can adopt the cross-sectional size and shape of the lumen of an injection applicator. In some embodiments, the dimensions of a tissue marker in a compact configuration can be comparable to or smaller than (e.g., by 1% or less, 5% or less or 10% or less) the lumen dimensions of an injection applicator. For example, if the injection applicator includes a needle, which has a lumen with a cylindrical cross-section, the flexible polymer matrix can adopt a cylindrical configuration with dimensions sufficient or small enough to fit inside the needle. In other embodiments, the tissue marker can exist in a compact configuration without the presence of any physical confinement. For example, the tissue marker can comprise a "smart" flexible polymer matrix (e.g., a woven or non-woven mat of coiled fibers) in a confined configuration, which can geometrically transform to an expanded configuration (e.g., a woven or non-woven mat of extended fibers) under a specific condition, e.g., a physiological condition (e.g., around body temperature).

By way of example only, in some embodiments where a flexible polymer film or sheet is rolled into a hollow cylinder and implanted in tissue at a target tissue site, the roll-up flexible polymer matrix, upon the implantation in the tissue, can unravel or unroll in order to conform to the space available at the target tissue site. In some embodiments, the roll-up flexible polymer matrix can partially unroll to an extent that it cannot expand further and its movement in at least one dimension is confined by the surrounding tissue. In other embodiments, the roll-up flexible polymer matrix can unroll completely to restore its original planar configuration (straight or bent) such that its movement in at least one dimension is confined by the surrounding tissue. In this instance, the expanded configuration refers to a partially-unrolled configuration or its original planar configuration, whereas the compact configuration refers to a rolled-up configuration prior to the implantation.

The transformation of the flexible polymer matrix from a compact configuration to an expanded configuration, while maintaining the density of the flexible polymer matrix, can occur instantaneously or gradually over a period of time, e.g., over a period of about 5 seconds, about 10 seconds, about 20 seconds, about 30 seconds, about 1 minute, about 5 minutes, about 10 minutes, about 15 minutes, or longer. After the tissue marker is in the expanded configuration and anchors or fixes at the implantation site, the injection applicator (e.g., but not limited to a needle cannula or catheter) used to implant the tissue marker can be withdrawn from the implantation site.

In accordance with some embodiments of this aspect and other aspects described herein, the tissue marker does not substantially migrate, upon implantation at a target tissue site, over an extended period of time. For example, the tissue marker does not substantially migrate, upon implantation at a target tissue site, over a period of at least about 2 weeks, at least about 3 weeks, at least about 1 month, at least about 2 months, at least about 3 months, at least about 4 months, at least about 5 months, at least about 6 months, at least at least about 7 months, at least about 8 months, at least about 9 months, at least about 10 months, at least about 11 months, at least about 12 months, at least about 2 years, at least about 3 years, at least about 4 years, at least about 5 years, at least about 6 years or longer. In some embodiments where the tissue marker is a permanent tissue marker, the tissue marker does not substantially migrate for a period as long as the tissue marker is maintained at the tissue target site in a subject.

As used herein, the phrase "does not migrate" or "does not substantially migrate" refers to tissue markers described herein moving a distance of no more than 10 mm from the target tissue site over a period of time, including, e.g., a distance of no more than 9 mm, no more than 8 mm, no more than 7 mm, no more than 6 mm, no more than 5 mm, no more than 4 mm, no more than 3 mm, no more than 2 mm, no more than 1 mm, no more than 0.5 mm, no more than 0.1 mm or less, from the target tissue site over a period of time. The period of time can range from days to weeks to years. In some embodiments, the period of time can be at least about 1 week, at least about 2 weeks, at least about 3 weeks, at least about 4 weeks, at least about 2 months, at least about 3 months, at least about 6 months, at least about 9 months, at least about 12 months, at least about 18 months, at least about 24 months or longer.

In some embodiments, the tissue marker does not migrate more than 5 mm (including, e.g., not more than 4 mm, not more than 3 mm, not more than 2 mm, not more than 1 mm or less) for a period of at least about 1 month or longer, including, e.g., at least about 2 months, at least about 3 months, at least about 6 months, at least about 9 months, at least about 1 year or longer.

In some embodiments, the tissue marker does not migrate more than 10 mm (including, e.g., not more than 9 mm, not more than 8 mm, not more than 7 mm, not more than 6 mm, not more than 5 mm, not more than 4 mm, not more than 3 mm, not more than 2 mm, not more than 1 mm or less) for a period of at least about 2 years or longer.

Stated another way, the phrase "does not migrate" or "does not substantially migrate" can mean that movement of tissue markers described herein from an implantation site over a period of time is substantially less than movement of a reference tissue marker from the same implantation site over the same period of time. In some embodiments, the distance over which the tissue markers move from an implantation site over a period of time is at least about 10% or more, including, e.g., at least about 20%, at least about 30%, at least about 40%, at least about 50%, at least about 60%, at least about 70%, at least about 80%, at least about 90%, at least about 95% or more, less than the distance over which a reference tissue marker moves from the same implantation site over the same period of time. The period of time can range from days to weeks to years. In some embodiments, the period of time can be at least about 1 week, at least about 2 weeks, at least about 3 weeks, at least about 4 weeks, at least about 2 months, at least about 3 months, at least about 6 months, at least about 9 months, at least about 12 months, at least about 18 months, at least about 24 months or longer. A reference tissue marker can be a conventional or commercially available biopsy marker, e.g., a metal clip.

In some embodiments, the distance over which the tissue markers move from an implantation site during a period of at least about 1 month or longer, is at least about 10% or more, less than the distance over which a conventional biopsy marker, e.g., a metal clip, moves from the same implantation site during the same period of time.

In some embodiments, the long-term migration effect can be simulated by centrifuging for a period of time (e.g., about 16 hours) a tissue or tissue phantom implanted with a tissue marker described herein. In some embodiments, the tissue or tissue phantom can be centrifuged at a speed of about 2000 rpm. After centrifugation, a mammography can be performed on the tissue or tissue phantom to determine the distance the tissue marker has moved from the original placement (e.g., a biopsy cavity). In some embodiments, the tissue marker can move no more than 10 mm or less (including, e.g., no more than 5 mm, no more than 3 mm, or no more than 2 mm or less) from the original placement (e.g., a biopsy cavity) after the tissue implanted with the tissue marker has been centrifuged at a speed of about 2000 rpm for about 16 hours at room temperature.

Tissue markers described herein are implanted into tissue at a target tissue site. The target tissue site at which the tissue marker is to be implanted can be any site in a tissue to be marked. For example, the target tissue site can be at, or in close proximity to, a void space or cavity, a lesion, a wound, a biopsy site, a diseased tissue area, a tissue area to be diagnosed, or any combinations thereof. In some embodiments, the target tissue site can be at, or in close proximity to, the site of a first biopsy. In one embodiment, the target tissue site is at the site of a first biopsy. The site of the first biopsy can be a void space created after the first biopsy is performed, or alternatively, be a site in close proximity or adjacent to a tissue to be biopsied. Thus, in some embodiments, the methods described herein can be used to mark a first biopsy site or area in a tissue. In some embodiments, the methods can further comprise performing a first biopsy prior to implanting one or more tissue markers into the first biopsy area. In some embodiments, the methods can further comprise performing a first biopsy after implanting one or more tissue markers into a first area to be biopsied. In one embodiment, the methods described herein can be used to mark a biopsy site or area in a breast tissue.

In some embodiments where several biopsies, e.g., for different lesions, are performed over time or at the same time, more than one tissue markers described herein can be used to distinguish each biopsy site. For example, by implanting different tissue markers (e.g., with different shapes, dimensions, compositions and/or signal type/intensity) at each distinct biopsy site, the biopsy sites can be differentiated by at least one imaging modality. Accordingly, in some embodiments, the method can further comprise performing a second biopsy after implanting another tissue marker into the second biopsy area. In some embodiments, the method can further comprise performing a second biopsy after implanting another tissue marker into a second area to be biopsied.

In some embodiments, it may be desirable to not only be able to place and visualize (under one or multiple imaging modalities) multiple tissue or biopsy markers within or adjacent to a biopsy site in tissue, but also to be able to differentiate the tissue or biopsy markers such that a distinction between the tissue markers placed first, placed second, and/or placed at any and all subsequent instances, can be made. By way of example only, upon implantation at different target tissue sites within the same tissue, a practitioner can distinguish tissue marker A placed at a first tissue site from tissue marker B placed at a second site. The tissue markers can be implanted at the same or different time. In some embodiments, the distinction between various tissue markers implanted at different instances (e.g., different sites and/or times) can be visualized due to a difference in signal intensity detected under at least one or more imaging modalities. In some embodiments, the distinction between the tissue markers can be visualized due to a difference in signal intensity under ultrasound, MRI, or x-ray, or any combination thereof. By way of example only, a difference in signal intensity as a means to differentiate various tissue markers described herein under MRI is exemplified in FIG. 4B and FIGS. 14A-14B, whereby the amount of a MRI-detectable contrast agent (e.g., iron oxide) controls the signal intensity and/or artifact size. As another example, a difference in shape or signal intensity as a means to differentiate various tissue markers described herein under X-ray is exemplified in FIGS. 2C-2D, whereby the amount of a radiocontrast agent, or the length of wire, differs to offer a difference in signal intensity or artifact size. In some embodiments, the variation in ultrasound intensity can be due to use of varying amounts of gas-filled bubbles, or absence of gas-filled bubbles in some tissue markers can serve as a means of differentiating tissue markers with gas-filled bubbles from those without gas-filled bubbles. Additionally or alternatively, various shapes and/or dimensions of a metal wire can be used, including but not limited to a flat, rectangular ribbon shape, a cylindrical wire, a rectangular bar shape, a bullet shape, a hour glass shape, a cross shape, or any irregular shape.

Unlike existing and conventional tissue markers, the tissue markers described herein, upon implantation, do not migrate away from the target tissue site (or implantation site) over an extended period of time, thus providing a more accurate location of the implantation site for future reference, biopsy, examination and/or optimized/targeted treatment planning. Accordingly, the method described herein, in some embodiments, can further comprise determining the location of the implanted tissue marker in the tissue at a first time point.

The first time point to determine the location of the implanted tissue marker in the tissue can be taken any time after the implantation of the tissue marker, e.g., whenever the target tissue site is needed to be located, e.g., for biopsy, examination and/or treatment. In some embodiments, the first time point to determine the location of the implanted tissue marker in the tissue can be taken immediately after the implantation of the tissue marker, e.g., within about an hour, within about 30 mins, within about 15 mins, within about 10 mins, within about 5 mins or less. In some embodiments, the first time point to determine the location of the implanted tissue marker in the tissue can be taken shortly after the implantation of the tissue marker, e.g., at least about one hour, at least about 2 hours, at least about 3 hours, at least about 4 hours, at least about 6 hours, at least about 9 hours, at least about 12 hours, at least about 16 hours, at least about 24 hours, at least about 2 days, at least about 3 days, at least about 4 days, at least about 5 days, at least about 6 days, at least about 1 week upon the implantation of the tissue marker. The first time point taken immediately or shortly after the implantation of the tissue marker can be used as a reference point, e.g., for future comparison when the tissue at, or in close proximity to, the implanted tissue marker is examined at a subsequent time point.

In some embodiments, the first time point to determine the location of the implanted tissue marker in the tissue can be taken at least about 1 week, at least about 2 weeks, at least about 3 weeks, at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months upon the implantation of the tissue marker. In some embodiments, the first time point to determine the location of the implanted tissue marker in the tissue can be taken at least about 1 year, at least about 2 years, at least about 3 years, at least about 4 years, at least about 5 years or longer upon the implantation of the tissue marker.

In some embodiments, the method can further comprise determining the location of the implanted tissue marker in the tissue at a second time point, wherein the second time point is subsequent to the first time point. The second time point can be taken any time, e.g., ranging from minutes to years, after the first time point. In some embodiments, the second time point to determine the location of the implanted tissue marker in the tissue can be taken shortly after the implantation of the tissue marker, e.g., at least about one hour, at least about 2 hours, at least about 3 hours, at least about 4 hours, at least about 6 hours, at least about 9 hours, at least about 12 hours, at least about 16 hours, at least about 24 hours, at least about 2 days, at least about 3 days, at least about 4 days, at least about 5 days, at least about 6 days, at least about 1 week or longer, after the first time point, e.g., to confirm the site for surgical removal and/or treatment of the tissue.

In some embodiments, the second time point to determine the location of the implanted tissue marker in the tissue can be taken after a longer period of time, e.g., to monitor the condition of the tissue at, or in close proximity to the target tissue site marked by the tissue marker. In these embodiments, the second time point to determine the location of the implanted tissue marker in the tissue can be taken at least about 1 week, at least about 2 weeks, at least about 3 weeks, at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months or longer, after the first time point. In some embodiments, the second time point to determine the location of the implanted tissue marker in the tissue can be taken at least about 1 year, at least about 2 years, at least about 3 years, at least about 4 years, at least about 5 years or longer, after the first time point.

In some embodiments, the target tissue site or implantation site can be a biopsy site. By more accurately or reliably identifying the location of the previous biopsy site using the tissue markers described herein, repeated sampling of the same biopsy area can be minimized or avoided. Thus, in some embodiments, the method can further comprise determining the location of the first biopsy site marked by the tissue marker described herein. In some embodiments, the method can further comprise performing a second biopsy at a site different from the first biopsy site marked by the tissue marker. In some embodiments, the second biopsy can be performed at a site not proximal to the first biopsy site marked by the tissue marker. In some embodiments, the second biopsy can be performed in close proximity to, but not at, the first biopsy site marked by the tissue marker. The biopsy can be performed with any procedure known to one of skill in the art. For example, in one embodiment, the biopsy can be a stereotactic core biopsy, which is a biopsy procedure that uses a computer and imaging performed in at least two planes to localize a target lesion in three-dimensional space and guide the removal of tissue for examination. In some embodiments, the stereotactic core biopsy can be vacuum-assisted.

Marking a target tissue site with one or more tissue markers described herein can also facilitate treating and/or monitoring or examining a condition of the same tissue at, or in close proximity to, the target tissue site marked by the tissue marker(s). In these embodiments, the method can further comprise examining tissue marked by at least one tissue marker described herein at a first time point. In some embodiments, the method can further comprise examining the same tissue marked by the tissue marker(s) at a second time point, wherein said second time point is subsequent to the first time point. In some embodiments, the method can further comprise removing or treating the tissue at, or in close proximity to, the same target tissue site marked by the tissue marker at any time point that is after the tissue maker is implanted. For example, the tissue at, or in close proximity to, the same target tissue site marked by the tissue marker can be removed or treated at the first time point defined herein, at the second time point defined herein, or at a time point after the second time point when a skilled practitioner determines to remove or treat the tissue. In some embodiments where the tissue is diagnosed with cancer, the tissue can be treated with radiation, chemotherapy and/or surgical removal.

As used herein, the term "treating" refers to therapeutic treatment wherein the purpose is to prevent or slow the development of the disease, e.g., cancer. Treatment is generally "effective" if one or more symptoms or clinical markers are reduced as that term is defined herein. Alternatively, a treatment is "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of extent of disease, stabilized (e.g., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with a disease or disorder (e.g., cancer), as well as those likely to develop a disease or disorder (e.g., cancer) based on the biopsy results.

As used herein throughout the specification, the term "close proximity" generally refers to the spatial distance of a target site from a reference site being no more than 5 cm, including, e.g., no more than 4 cm, no more than 3 cm, no more than 2 cm, no more than 1 cm, no more than 0.5 cm, no more than 0.1 cm or less. Accordingly, the term "close proximity," when used in reference to the spatial relationship between target tissue site and the site of a first biopsy, refers to a spatial distance of the target tissue site from the site of a first biopsy being no more than 5 cm, no more than 4 cm, no more than 3 cm, no more than 2 cm, no more than 1 cm, no more than 0.5 cm, no more than 0.1 cm or less. When used in reference to the spatial relationship between a second biopsy site and the target tissue site marked by the tissue marker, the term "close proximity" refers to a spatial distance of a second biopsy from the target tissue site marked by the tissue marker being no more than 5 cm, no more than 4 cm, no more than 3 cm, no more than 2 cm, no more than 1 cm, no more than 0.5 cm, no more than 0.1 cm or less. When used in reference to the spatial relationship between a tissue examination, removal or treatment site and the target tissue site marked by the tissue marker, the term "close proximity" refers to a spatial distance of a tissue examination or treatment site from the target tissue site marked by the tissue marker being no more than 5 cm, no more than 4 cm, no more than 3 cm, no more than 2 cm, no more than 1 cm, no more than 0.5 cm, no more than 0.1 cm or less.

As the flexible polymer matrix of the tissue markers according to one or more embodiments described herein can further comprise macropores, the method can further comprise growing a plurality of cells into the macropores. In some embodiments, at least one of the plurality of cells can infiltrate or migrate from the surrounding tissue. Without wishing to be bound by theory, in some embodiments, anchorage of the tissue marker at the tissue marker site can be reinforced by growing the plurality of cells into the macropores, e.g., to allow cells from the surrounding tissue to infiltrate the macropores where the infiltrating cells can proliferate and expand to become a plurality of cells.

Without wishing to be limiting, in some embodiments, tissues markers comprising macropores can be used as a scaffold. For example, the tissue markers described herein can be used to collect cells from tissues surrounding the implantation site, and/or to facilitate tissue integration and/or regeneration at the target tissue site. Accordingly, in another aspect, a method, e.g., of producing a scaffold comprising a population of cells is also provided herein. The method can comprise (a) implanting into tissue at a target tissue site a tissue marker having a flexible polymer matrix arranged in a compact configuration, wherein the flexible polymer matrix comprises macropores and has a density substantially the same as the tissue, and wherein upon the implantation at the target tissue site, the flexible polymer matrix transforms from the compact configuration to an expanded configuration while maintaining the density, and (b) growing a plurality of cells into the macropores, wherein the tissue is not an eye tissue or a lens capsule. In some embodiments, the tissue markers described herein can be implanted in a soft tissue, including, e.g., but not limited to, a breast, colon, rectal, liver, ovarian, prostate or lung tissue. In one embodiment, the tissue amenable to the method described herein can be a breast tissue.

In some embodiments, at least one of the plurality of cells can infiltrate or migrate from the surrounding tissue into the macropores, where the infiltrating cell can proliferate and expand to a plurality of cells.

In some embodiments of this aspect described herein, the method can further comprise implanting cells at the target tissue site where the tissue marker is implanted. In some embodiments, the methods can further comprise seeding a plurality of cells into the macropores of the tissue marker. The cells that are implanted at the target tissue site or seeded into the macropores can typically be the same cell types as the cells residing in the tissue.

In some embodiments, the tissue marker is implanted without the use of an adhesive as described earlier. In some embodiments, the tissue marker is secured or fixed at the target tissue site without the use of an adhesive as described earlier.

In some embodiments of various aspects described herein, the methods can be used to deliver at least one or more active agents as described herein. In these embodiments, the active agent(s) can be pre-loaded into or pre-coated onto the tissue marker or the flexible polymer matrix. Additionally or alternatively, the active agent(s) can be administered to the target tissue site prior to, concurrently with, or after the implantation of the tissue marker. In one embodiment, the active agent(s) can be administered to the target tissue site by injection.

The methods of this aspect and other aspects described herein can generally be applicable to any types of tissue in a subject, wherein the tissue is not an eye or ocular tissue, including a lens capsule. In some embodiments, the tissue amenable to the methods of various aspects described herein can be a soft tissue, e.g., adipose tissue, breast tissue, colon tissue, rectal tissue, liver tissue, ovarian tissue, prostate tissue, or lung tissue. In one embodiment, the tissue amenable to the methods of various aspects described herein is a breast tissue.

Tissue Markers Described Herein

In accordance with various embodiments described herein, the tissue markers employed in the methods of various aspects described herein comprises a flexible polymer matrix adapted to be capable of transforming from a compact configuration to an expanded configuration, and has a density substantially the same as a tissue, in which the tissue markers are to be implanted. An exemplary tissue marker is shown in FIG. 1.

As used herein, the term "flexible" generally refers to a material being capable of bending or flexing such that it is pliant and yieldable in response to a change in surrounding condition (e.g., an applied force), without causing any macroscopic breaking. A flexible material can generally alter geometric shape and/or geometric structure to accommodate a change in surrounding condition and to conform or adjust to the shape of an object brought in contact with it without losing its integrity. Thus, the term "flexible" when used in reference to a polymer matrix of the tissue markers described herein refers to a polymer matrix being capable of altering its geometric shape and geometric structure in response to a change in surrounding condition without losing its integrity and/or causing any macroscopic breaking. For example, the polymer matrix of the tissue markers described herein is flexible enough to permit transformation from a compact configuration to an expanded configuration as described herein.

To minimize the movement of the tissue markers in a target tissue over time upon implantation, the density (material density) of the flexible polymer matrix is substantially the same as a target tissue, in where the tissue marker is to be implanted. In some embodiments, the densities (material densities) of the flexible polymer matrix and the target tissue can differ by no more than 30% of the tissue density, including no more than 20%, no more than 10%, no more than 9%, no more than 8%, no more than 7%, no more than 6%, no more than 5%, no more than 4%, no more than 3%, no more than 2%, no more than 1% or less, of the tissue density.

In some embodiments, in order to further minimize the movement of the tissue markers in a target tissue upon implantation, the flexible polymer matrix can have an electrostatic pressure (e.g., force per area that an electrical charge exerts on an object) substantially the same as a target tissue, in where the tissue marker is to be implanted. In some embodiments, the electrostatic pressure of the flexible polymer matrix and the target tissue can differ by no more than 30% of the tissue electrostatic pressure, including no more than 20%, no more than 10%, no more than 9%, no more than 8%, no more than 7%, no more than 6%, no more than 5%, no more than 4%, no more than 3%, no more than 2%, no more than 1% or less, of the tissue electrostatic pressure.

In some embodiments of various aspects described herein, the flexible polymer matrix can further comprise at least one macropore (e.g., void space), including, e.g., at least two, at least three, at least four, at least five or more macropores. In some embodiments, these macropores can be adapted to provide sites for cell seeding, cell infiltration, cell growth and/or cell proliferation, which can, e.g., provide additional anchorage of the tissue marker at the implantation site and/or to form a cell scaffold. In some embodiments, the macropores can form channels between two opposing or apposing surfaces of the flexible polymer matrix. For example, the macropores can penetrate through the entire thickness of the flexible polymer matrix, e.g., forming holes or channels through the entire thickness of the flexible polymer matrix. The channels of the macropores can each independently have a cross-section of any shape, e.g., but not limited to, circular, oval, elliptical, triangle, square, rectangle, polygon, or any irregular shapes. In one embodiment, the channels of the macropores can have a circular cross-section.

In some embodiments, the macropores do not necessarily penetrate through the entire thickness of the flexible polymer matrix. For example, the macropores can form indentations on surfaces of the flexible polymer matrix. In some embodiments, the macropores can form an interconnected network of pores within the flexible polymer matrix.

The macropores can each independently have a cross-sectional dimension (e.g., diameter for a circular cross-section, or length for a square cross-section) of any size sufficient for at least one or more cells to reside and/or populate therein, depending on, e.g., cell size, and/or number of cells to be desired to grow therein. In some embodiments, the macropores can each independently have a cross-sectional dimension of about 50 μm to about 1000 μm, about 100 μm to about 1000 μm, or about 200 μm to about 900 μm, or about 300 μm to about 800 μm, or about 400 μm to about 700 μm. In some embodiments, the macropores can each independently have a cross-sectional dimension of about 0.2 mm to about 3 mm, or about 0.5 mm to about 2 mm, or about 1 mm to about 2 mm.

The macropores can be present in any number and/or in any arrangement within the flexible polymer matrix. The number of the macropores present in the flexible polymer matrix can vary with the size of the macropores, the size and/or the mechanical property (e.g., flexibility) of the flexible polymer matrix (without macropores), desired porosity of the flexible polymer matrix, and any combinations thereof. The term "porosity" is generally a measure of void spaces in a material, and is a fraction of volume of voids over the total volume, as a percentage between 0 and 100% (or between 0 and 1). With respect to a planar structure, e.g., a film, the term "porosity" can be measured as a fraction of projected surface area of voids over the total projected surface area, e.g., as a percentage between 0% and 100% (or between 0 and 1). In some embodiments, the flexible polymer matrix can have a plurality of macropores that yields the flexible polymer matrix with a porosity of less than 50%, less than 40%, less than 30%, less than 20%, less than 10%, less than 5%, less than 3%, less than 2%, less than 1% or lower.

The flexible polymer matrix can be fabricated into any format before it is adapted to form a compact configuration for use in the methods described herein. In some embodiments, the flexible polymer matrix can be fabricated into a film, a sheet, a network of fibers such as a woven or non-woven mat, a hollow cone, a hollow polyhedron, a hollow pyramid, a hollow cylinder, any 2-D planar structures, or any 3-D hollow structures, or any combinations thereof. In some embodiments, the flexible polymer matrix is not in a form of a foam or sponge. In some embodiments, the flexible polymer matrix is not in a form of an inflatable balloon. In some embodiments, the flexible polymer matrix can be fabricated into a film, e.g., a solid film. In order to maintain the flexibility of the polymer matrix for the methods described herein, the film, e.g., a solid film, can have an appropriate thickness that yields a flexible polymer matrix, e.g., being capable of transforming from a compact configuration to an expanded configuration in response to the changes in surrounding space, e.g., degree of confinement. In some embodiments, the film can have a thickness of about 0.05 mm to about 4 mm, or about 0.1 mm to about 3 mm, or about 0.5 mm to about 2 mm. Without limitations, the film can be in any shape, e.g., a triangle, a square, a rectangle, a circle, a polygon, or an irregular shape.

In some embodiments, the flexible polymer matrix can comprise an agent or material that enhances the flexibility or elasticity of the selected polymer material(s) and/or the transformation between the compact configuration and the expanded configuration. In one embodiment, the agent that enhances the flexibility or elasticity of the selected polymer material(s) and/or the transformation between the compact configuration and the expanded configuration includes at least one shape-memory alloy material and/or at least one elastic material. Exemplary shape-memory alloy material and/or elastic material includes, but is not limited to, copper-aluminum-nickel alloys, nickel-titanium (NiTi) alloys or nitinol, alloys comprising at least two or more of zinc, copper, gold and iron, and any combinations thereof. The shape-memory alloy material and/or elastic material can be provided in any shape, e.g., but not limited to, straight or curved wire, ribbon, coil, an intertwining structure, or any combinations thereof. In one embodiment, the flexible polymer matrix can comprise at least one or more nitinol wires. In some embodiments, by changing the dimensions (e.g., lengths, thickness) and/or shapes of the shape-memory alloy materials and/or elastic materials (e.g., but not limited to a nitinol wire) included in the tissue markers, different tissue markers described herein can acquire unique appearances and/or produce unique signals under at least one imaging modality.

The dimensions and/or shape of the flexible polymer matrix can depend upon various factors, including, e.g., but not limited to, types of applications, types of imaging modalities used (including, e.g., imaging resolution, operating parameters), size of target tissue site or void, and/or methods of implantation. For example, in some embodiments, the dimensions and/or shape of the flexible polymer matrix can be selected so as to accommodate the dimensions and/or shape of a particular implantation device or applicator. In one embodiment, by selecting the dimensions and/or shape of the flexible polymeric matrix such that its compact configuration can fit within the internal diameter of an injection applicator, e.g., a biopsy needle, the tissue marker can be implanted or applied to the target tissue site during or after the course of a biopsy procedure. For example, the flexible polymer matrix can have a size and shape selected to permit application of the tissue marker having the flexible polymer matrix in its compact configuration through the hollow interior space of a breast biopsy device, e.g., HOLOGIC® ATEC or HOLOGIC® EVIVA. In some embodiments, the dimensions of the flexible polymer matrix can be selected so as to be large enough in its expanded configuration to provide a distinct, recognizable marker image at the target tissue site (e.g., a biopsy site), when visualized under a particular imaging system and operating conditions of use. In some embodiments, the dimensions of the flexible polymer matrix can be selected to be small enough in its expanded configuration to avoid masking or obscuring diagnostically important tissue features. By way of example only, when the flexible polymer matrix is fabricated into a film, in some embodiments, the film can have a dimension of about 0.2 cm to about 2 cm, or about 0.5 cm to about 2 cm, or about 0.5 cm to about 1.5 cm.

In some embodiments, the flexible polymer matrix is not a gel matrix or a hydrogel.

The flexible polymer matrix can comprise at least one or more polymeric materials. In some embodiments, the flexible polymer matrix can comprise at least two, least three, at least four or more polymeric materials. In some embodiments, the polymer material forming the flexible polymer matrix can be biodegradable or non-biodegradable. In some embodiments, the flexible polymer matrix can comprise at least one or more biodegradable polymeric material, or at least one non-biodegradable material, or a combination thereof.

As used herein, the term "biodegradable" refers to the ability of a polymeric material to erode or degrade in vivo to form smaller chemical fragments. Degradation may occur, for example, by enzymatic, chemical or physical processes. Non-limiting examples of biodegradable polymeric materials that can be used to form a flexible polymer matrix can include polyester, polyamide, polycarbonates, polyanhydrides, polyorthoesters, polycaprolactone, polyesteramides, polycyanoacrylate, polyetherester, poly(phosphates), poly(phosphonates), poly(phosphites), polyhydric alcohol esters, blends and copolymers thereof.

As used herein, the term "non-biodegradable" refers to the ability of a polymeric material to resist erosion or degradation in vivo. Thus, a non-biodegradable material can stay in vivo for a significantly long amount of time, or even permanently. Non-limiting examples of degradation-resistant polymeric materials suitable for use in the flexible polymer matrix can include polyethylene, polypropylene, polytetrafluoroethylene, polyurethanes, silicon, polyacrylates, ethylene-vinyl acetates (and other acyl-substituted cellulose acetates), polystyrenes, polyvinyl oxides, polyvinyl fluorides, poly(vinyl imidazoles), chlorosulphonated polyolefins, polyethylene oxides, polyvinyl alcohols (PVA), any art-recognized degradation-resistant polymers, or any combinations thereof.

In some embodiments, the polymeric material forming the flexible polymer matrix can comprise at least one viscoelastic polymer. As used herein, the term "viscoelastic" refers to a polymeric material exhibiting both elastic and viscous characteristics. For example, a viscoelastic polymeric material can at least partially return to its original form when an applied stress is released, and the response is time-dependent. In dynamic mechanical characterization, the level of viscoelasticity is proportional to the damping coefficient measured by the tan delta of the material. The tan delta is generally the ratio of the viscous dissipative loss modulus G" to the elastic storage modulus G'. High tan delta values can indicate a high viscous component in the material behavior and hence a strong damping to any perturbation will be observed. The measurement of these moduli is described in An Introduction to Rheology, by H. A. Barnes, J. F. Hutton, and K. Walters, Elsevier, Amsterdam (1997).

In some embodiments, the polymeric material forming the flexible polymer matrix can comprise at least one elastic polymer or elastomer. The terms "elastic polymer" and "elastomer" as used interchangeably herein, generally refer to a polymeric material having low Young's modulus and high yield strain compared with other types of polymeric materials. In some embodiments, the elastic polymer or elastomer can include rubber. Exemplary elastomers can include, without limitations, synthetic polyisoprene, polybutadiene, chloroprene rubber, polychloroprene, neoprene, baypren, butyl rubber (e.g., copolymer of isobutylene and isoprene), halogenated butyl rubbers (e.g., chloro butyl rubber; bromo butyl rubber), styrene-butadiene rubber (copolymer of styrene and butadiene), nitrile rubber (copolymer of butadiene and acrylonitrile), hydrogenated nitrile rubbers, ethylene propylene rubber, ethylene propylene diene rubber, epichlorohydrin rubber, polyacrylic rubber, silicone rubber, fluorosilicone rubber, fluoroelastomers, perfluoroelastomers, polyether block amides, chlorosulfonated polyethylene, ethylene-vinyl acetate, and any combinations thereof.

In some embodiments, the polymeric material forming the flexible polymer matrix can comprise at least one shape memory polymer. As used herein, the term "shape memory polymer" refers to a polymeric material that is stimuli-responsive. Upon application of an external stimulus, a shape memory polymer has the ability to change their geometric configuration, e.g., from a coil to a partially or fully unwrapped coil. By way of example only, a change in shape initiated by a change in temperature (e.g., a change in temperature from room temperature to a subject's body temperature, e.g., ~37° C. for human beings) can be referred to as a thermally induced shape memory effect. Examples of thermally-induced shape memory polymer can include, but are not limited to, polyurethanes, polyurethanes with ionic or mesogenic components, block copolymer of polyethylene terephthalate (PET) and polyethyleneoxide (PEO), block copolymers containing polystyrene and poly(1,4-butadiene), and an ABA triblock copolymer made from poly(2-methyl-2-oxazoline) and polytetrahydrofuran. Additional examples of shape memory polymer that can be applicable in the tissue markers described herein include the ones described in the International App. No. WO 2008/014109, the content of which is incorporated herein by reference.

In some embodiments, the flexible polymer matrix can further comprise dispersed or incorporated iron oxide nanoparticles.

In some embodiments of various aspects described herein, the tissue markers described herein can be adapted to be readily detected by at least one imaging modality. In some embodiments, the flexible polymer matrix can be adapted to be detectable by at least one imaging modality. In some embodiments, the tissue marker or flexible polymer matrix can be adapted to be detectable by at least two or more imaging modalities. In some embodiments, the tissue marker or flexible polymer matrix can be adapted to be detectable by least three or more imaging modalities. Non-limiting examples of imaging modalities that can be used to detect the tissue markers can include, but are not limited to, magnetic resonance imaging, mammography, X-ray-based imaging, ultrasound imaging, fluorescence imaging, computed tomography imaging and any combinations thereof. Additional examples of imaging modalities that can be used to detect the tissue markers can include, but are not limited to, portal film imaging, electronic portal imaging, electrical impedance tomography (EIT), magnetic source imaging (MSI), magnetic resonance spectroscopy (MRS), magnetic resonance mammography (MRM), magnetic resonance angiography (MRA), magnetoelectro-encephalography (MEG), laser optical imaging, electric potential tomography (EPT), brain electrical activity mapping (BEAM), arterial contrast injection angiography, and digital subtraction angiography modalities. Nuclear medicine modalities include positron emission tomography (PET) and single photon emission computed tomography (SPECT). In one embodiment, the flexible polymer matrix can be adapted to be detectable by at least magnetic resonance imaging, X-ray-based imaging, and ultrasound imaging.

In some embodiment where the tissue markers are detectable by at least one imaging modality, the flexible polymer matrix can be adapted to suit for a specific imaging modality. For example, in some embodiments, at least one material forming the flexible polymer matrix can produce a signal detectable by at least a first imaging modality. Where the first imaging modality involves ultrasound imaging, at least one material forming the flexible polymer matrix can include, but not limited to, polyethylene, polypropylene, polytetrafluoroethylene, polyurethanes, polyester, polyamide (e.g., nylon-6, nylon-6,6, nylon-12), polycarbonate and any combination thereof. In other embodiments, at least one material forming the flexible polymer matrix can include a radiopaque polymer, e.g., silicon, polycarbonate resin, or a combination thereof. As used herein, the term "radiopaque" refers to a characteristic of a polymer material being able to be detected by X-ray analysis.

In some embodiments, the flexible polymer matrix can comprise at least one contrast agent (including, e.g., at least two, at least three, at least four or more contrast agents) detectable or visible by at least one imaging modality. The contrast agent(s) can be coated on the flexible polymer matrix, and/or mixed, embedded, dispersed, or suspended homogenously or heterogeneously in the flexible polymer matrix. In some embodiments, the contrast agent(s) can be dispersed uniformly or homogeneously throughout the flexible polymer matrix. In other embodiments, the contrast agent(s) can be localized at a certain location within the flexible polymer matrix.

The contrast agent can be gas, liquid, solid, gel, or any combinations thereof. Depending on types of the selected imaging modalities, the contrast agent can be selected to produce a change in signal intensity under at least one or more imaging modalities, and/or to provide visibility under at least one or more imaging modalities. For example, the contrast agent(s) can be independently selected to produce a decrease in signal intensity under MRI, and/or it can be selected to provide visibility under x-ray and/or ultrasound imaging.

Figure 14A:
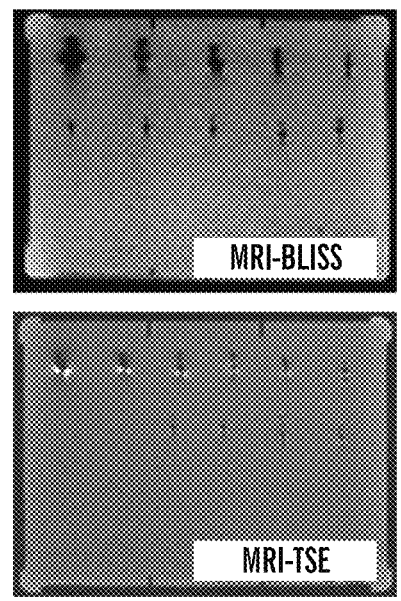
FIGS. 14A-14B are experimental data showing size artifacts (volume) of exemplary tissue markers described herein as a function of iron oxide content per $cm^2$ of the tissue marker film.
Figure 14B:
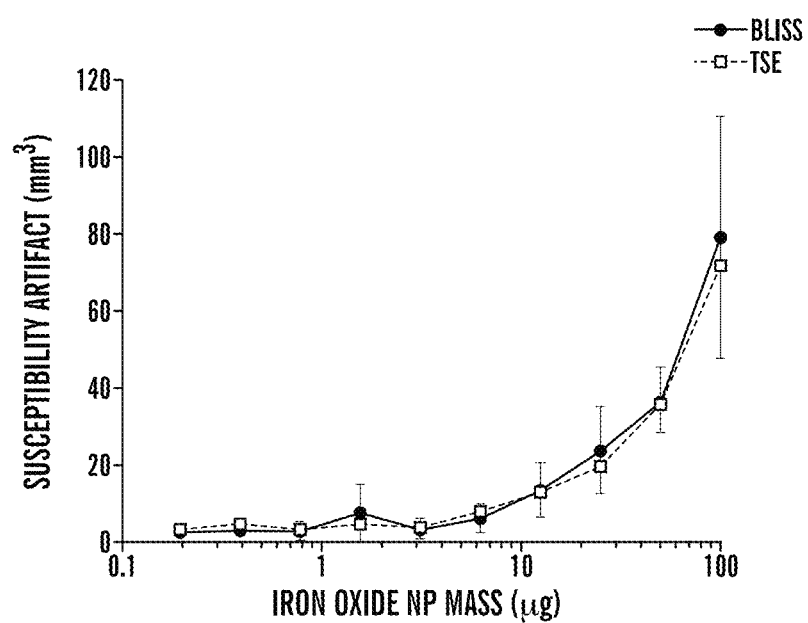

The amount of each contrast agent can be adjusted for types of contrast agents used, degree of visibility of contrast agents, imaging artifacts, and/or sensitivity of imaging systems. For example, as shown in FIG. 2C and FIG. 4B, various amounts of iodinated salts (e.g., ranging from about 60 µg to about 8000 µg) and iron oxide nanoparticles (e.g., ranging from about 0.1 µg to about 500 µg) can be loaded into the flexible polymer matrix to enhance the signal intensity of X-ray imaging and MRI imaging, respectively. In some embodiments, the amount of each contrast agent can be calibrated to minimize artifact size or volume resulted from detection by a selected imaging modality. For example, FIGS. 14A-14B shows the dependence of artifact size (volume) on iron oxide content in the flexible polymer matrix. Accordingly, one of skill in the art can determine appropriate amounts of different contrast agents used in the tissue marker. In one embodiment, the optimum iron oxide content can be determined using the method as described in Example 10.

In some embodiments, the amount of a contrast agent present in the flexible polymer matrix can vary from about 0.1 µg/cm$^2$ to about 500 µg/cm$^2$. In some embodiments, the amount of iodinated salts distributed in the flexible polymer matrix can vary from 60 µg/cm$^2$ to about 8000 µg/cm$^2$. In some embodiments, the amount of iron oxide nanoparticles distributed in the flexible polymer matrix can vary from 0.1 µg/cm$^2$ to about 500 µg/cm$^2$. In some embodiments, the amount of iron oxide nanoparticles distributed in the flexible polymer matrix can vary from 0.1 µg/cm$^2$ to about 250 µg/cm$^2$. In some embodiments, the amount of iron oxide nanoparticles distributed in the flexible polymer matrix can vary from 0.1 µg/cm$^2$ to about 100 µg/cm$^2$.

By way of example only, in some embodiments, the flexible polymer matrix can comprise at least one contrast agents detectable by at least magnetic resonance imaging (MRI). Such MRI-detectable contrast agent(s) can have a magnetic susceptibility substantially comparable to a target tissue, in which the tissue marker is to be implanted; or it can comprise a paramagnetic material that can induce T1 relaxivity yielding an increased signal on T1-weighted MRI or a decreased signal on T2-weighted MRI. Examples of MRI contrast agent(s) suitable for use in the tissue markers described herein can include, but are not limited to, metal oxide particles (e.g., iron oxide nanoparticles), metal materials, amorphous materials, crystalline materials, gadolinium, and any combinations thereof. In one embodiment, the flexible polymer matrix can comprise metal oxide particles or nanoparticles (e.g., iron oxide nanoparticles) as a MRI contrast agent. In one embodiment, the flexible polymer matrix can comprise a metal material (e.g., nitinol) in any form, e.g., but not limited to, a wire, a clip, a coil, particles, or any combinations thereof, as a MRI contrast agent.

Additionally or alternatively, the flexible polymer matrix can comprise at least one or more contrast agents detectable by at least X-ray imaging, e.g., a radiopaque material (e.g., Ioxaglate or iodine (HEXABRIX® or CYSTO CONRAY-TMII), bromine, salts (e.g., an iodinated salt, barium salts (e.g., barium sulfate), bismuth salts (e.g., bismuth oxychloride), or any combinations thereof), metal or alloy materials (e.g., nitinol, titanium, tantalum, tungsten, stainless steel, platinum, gold, iridium, silver, rhodium, nickel, or any combinations thereof), metal oxide particles or nanoparticles, and any combinations thereof. In one embodiment, the flexible polymer matrix can comprise an iodinated salt (e.g., potassium iodide) as an X-ray contrast agent. In one embodiment, the flexible polymer matrix can comprise Ioxaglate (e.g., HEXABRIX®) as an X-ray contrast agent. In one embodiment, the flexible polymer matrix can comprise a metal material (e.g., nitinol or titanium) in any form, e.g., but not limited to, a wire, a clip, a coil, particles, or any combinations thereof, as an X-ray contrast agent. In one embodiment, the flexible polymer matrix can comprise a nitinol wire.

In some embodiments, a selected contrast agent to be included in the flexible polymer matrix can be detectable by at least two or more imaging modalities. For example, metal or alloy materials (e.g., nitinol) can be detectable by at least both MRI and X-ray imaging. Gas bubbles embedded in the polymer matrix, for example, can be also detectable by ultrasound imaging. For example, Vitamin E or manganese, or other paramagnetic substances embedded in the polymer matrix can cause a positive signal (increase in signal intensity) on the MR image.

In some embodiments, the contrast agent(s) can be formed by integrating at least two or more contrast agents to form an integral entity. In some embodiments, the contrast agent(s) can comprise a first contrast agent and a second contrast agent, forming an integral entity. By way of example only, the contrast agent can comprise iron oxide nanoparticles coated with another contrast agent, e.g., an iodinated salt, compound, or molecule.

In some embodiments, the contrast agent(s) can be deposited on the tissue markers described herein. The contrast agent(s) can be deposited on the tissue markers in any desirable pattern. Examples of patterns include, but are not limited to, alphabets, numbers, symbols, or any combinations thereof. In one embodiment, the contrast agent(s) can be deposited on the tissue markers in a pattern comprising at least one alphabet, or at least one numerical digit, or at least one symbol, or any combinations thereof. In one embodiment, the contrast agent(s) can be deposited on the tissue markers in a pattern that can act as an identification tag for the respective tissue markers. Thus, different tissue markers implanted in a tissue can be differentiated accordingly. The contrast agent(s) can be deposited on the tissue markers using any methods known in the art, including, e.g., but not limited to, micropatterning or inkjet printing.

In some embodiments, the flexible polymer matrix can further comprise a signal enhancer, e.g., to increase the signal intensity and/or visibility of the tissue marker detected by a selected imaging modality. For example, a signal enhancer can be selected to be included in the flexible polymer matrix such that a difference in acoustic impedance between the flexible polymer matrix and the signal enhancer can cause the tissue marker to reflect ultrasound waves, thereby promoting the visibility of the tissue marker in an ultrasound imaging modality. In one embodiment, the flexible polymer matrix can further comprise a plurality of gas-filled microbubbles adapted to provide high reflectivity of the incident ultrasound energy. In such embodiments, the gas-filled microbubbles are surfactant-stabilized. In some embodiments, the diameter of the gas-filled microbubbles can typically range from about 1 micrometer, to about 100 micrometers, or from about 5 micrometers to about 40 micrometers. Examples of a gas used to form microbubbles include, but are not limited to, air, nitrogen, oxygen, carbon dioxide, argon, helium, perfluorocarbon gases, and any combinations thereof. In one embodiment, the gas used to form microbubbles is not carbon dioxide.

In some embodiments, the tissue markers described herein do not include any adhesive or sealant component that can cause the flexible polymer matrix or the marker body to adhere to adjacent or surrounding tissue at the target tissue site. Examples of an adhesive or sealant component that are absent in the tissue markers described herein can include, but are not limited to, a polyurethane compound, a polyacrylic compound, polyhydroxymethacrylate, a fibrin glue or sealant (e.g., TISSEAL™), collagen adhesive, or any combinations thereof.

In some embodiments, the tissue marker or the flexible polymer matrix can further comprise at least one or more active agent(s). The active agent(s) can be selected to provide a desired therapeutic or prophylactic effect. For example, in some embodiments, the active agent(s) can be selected to promote angiogenesis, cell proliferation, cell differentiation, wound healing and/or tissue regeneration; and/or to inhibit inflammation, infection, and/or growth of transformed (cancerous) cells. Examples of an active agent include, but are not limited to a therapeutic agent, a radioisotope for radiation therapy, a chemotherapeutic, an antimicrobial agent (e.g., antibiotics or an antiseptic agent), an anesthetic, a cell growth factor, a peptide, a peptidomimetic, an antibody or a portion thereof, an antibody-like molecule, nucleic acid, a wound healing agent, and any combinations thereof. In one embodiment, the active agent to be delivered to the target tissue site and/or surrounding tissue can comprise an antimicrobial agent (e.g., antibiotics or an antiseptic agent). Additional examples of an active agent can include growth factors, e.g., but not limited to, heparin binding growth factor (HBGF), transforming growth factor alpha or beta (TGF-beta), alpha fibroblastic growth factor (FGF), epidermal growth factor (TGF), vascular endothelium growth factor (VEGF); hormones, e.g., but not limited to, insulin, glucagon, and estrogen; therapeutic agents or drugs, e.g., but not limited to wound-healing agents, anti-inflammatory steroids and non-steroidal anti-inflammatory drugs; chemotherapeutics; antimicrobial agents; an anesthetic, and any combinations thereof.

The term "antimicrobial agent" as used herein refers to any entity with antimicrobial activity, i.e. the ability to inhibit or reduce the growth and/or kill a microbe, for example, bacteria. In various embodiments, the antimicrobial agent can be a compound (e.g., antibiotics or antiseptic agent) indicated for treatment of a bacterial infection in a human or veterinary subject.

In some embodiments, an antimicrobial agent can be an antibiotic. As used herein, the term "antibiotic" is art recognized and includes antimicrobial agents naturally produced by microorganisms such as bacteria (including *Bacillus* species), actinomycetes (including *Streptomyces*) or fungi that inhibit growth of or destroy other microbes, or genetically-engineered thereof and isolated from such natural source. Substances of similar structure and mode of action can be synthesized chemically, or natural compounds can be modified to produce semi-synthetic antibiotics.

Active agents can be incorporated into the tissue marker or the flexible polymer matrix, e.g., as a coating of the flexible polymer matrix, and/or dispersed within the flexible polymer matrix. In some embodiments, the active agent(s) can be released over time by diffusion. In some embodiments, the active agents can be released by degradation of the biodegradable flexible polymer matrix. Additionally or alternatively, the active agent can be separately delivered to the target tissue site (e.g., by injection) prior to, concurrently with, or after the implantation of the tissue marker.

In some embodiments, the active agent(s) can be incorporated into the tissue marker or flexible polymer matrix between about 0.01% and about 80% by weight, or between about 1% and about 30%. One of skill in the art can determine an appropriate loading amount of active agent according to various applications and purposes.

Exemplary Methods of Fabricating Tissue Markers Described Herein

Figure 5A:
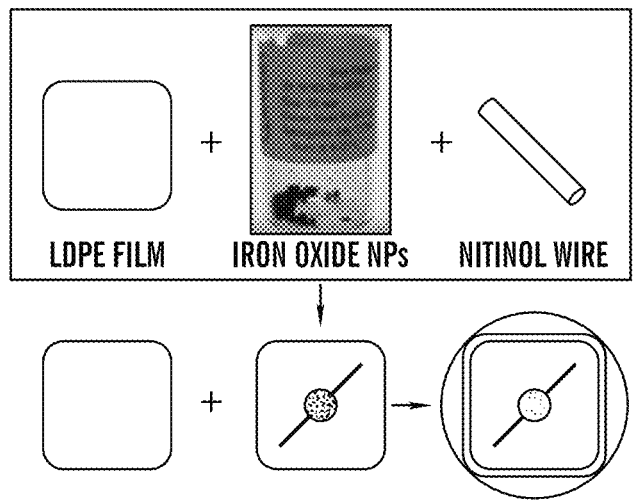
FIGS. 5A-5B are schematic diagrams showing two different methods of fabricating a tissue marker described herein.

Tissue markers described herein can be produced by any methods known in the art. In some embodiments, as shown in FIG. 5A, a tissue marker comprising one or more polymeric materials described herein (e.g., non-biodegradable polymers, biodegradable polymers, viscoelastic polymers, elastic polymers and any combinations thereof) and one or more contrast agents, can be mixed with heat to form a molten solution, suspension, or dispersion, and cooled in or through a mold or profile to produce a desired shape and size. Suitable melt-processing techniques include, but are not limited to, extrusion and compounding, hot-pressing, injection-molding, stamping, and thermoforming.

Figure 9A:
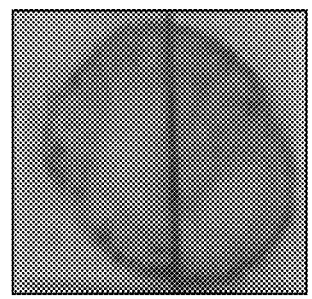
FIGS. 9A-9B are images of example tissue markers fabricated using different methods as described in the Examples.
Figure 9B:
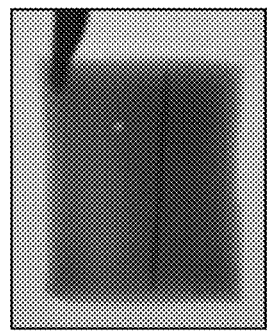

In some embodiments, the tissue markers described herein can be fabricated using a melt-processing sealing method, which comprises melting and sealing two polymeric films with at least one or more contrast agents sandwiched between the two polymeric films. In one embodiment, iron oxide particles and optionally a wire can be sandwiched between the two polymeric films. By way of example only, on the top of a pre-formed polymeric film (e.g., a polyethylene film) can be added iron oxide nanoparticles dissolved in an organic solvent (e.g., chloroform). The amount of iron oxide nanoparticles added to the polymeric film can vary with the size of polymeric film. The solvent is then allowed to evaporate, leaving the iron oxide particles behind. In some embodiments, a solution comprising an additional contrast agent (e.g., but not limited to, potassium iodide and/or barium sulfate) can be added on the top surface of the polymeric film, and excess solvent is then removed to leave the additional contrast agent behind. A piece of wire can be optionally placed on the top surface of the polymeric film with the nanoparticles residues disposed thereon. In one embodiment, the wire can be a piece of Nitinol wire of an appropriate diameter (e.g., ~0.003" diameter). As shown in FIG. 9A, the Nitinol wire can be placed at or around the center of the polyethylene film having nanoparticle residue disposed thereon. A second polymeric film of the same or different material (e.g., a polyethylene film) is subsequently added on top of the nanoparticle residue, and the two films are then sealed together by applying heat and pressure to melt the two films together along the entirety of their shared contact area.

Figure 5B:
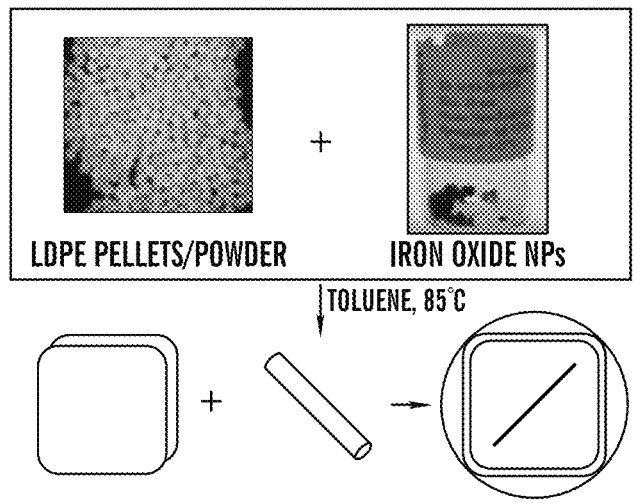
Figure 5B:

In alternative embodiments, as shown in FIG. 5B, a tissue marker described herein can be manufactured by a process comprising solvent casting. For example, one or more non-biodegradable and/or biodegradable polymers and one or more contrast agents can be mixed with an appropriate solvent to form a solution, suspension, or dispersion, and cast into a mold or placed atop a surface to produce a flexible polymer matrix of a desired shape and size.

In some embodiments, the tissue markers described herein can be fabricated using a solvent casting and melt sealing method, which comprises solvent casting a first polymeric film comprising at least one contrast agent distributed therein, and optionally entrapping one or more contrast agents between the first polymeric film and a second polymer film using a melt-sealing method. For example, a solution mixture of polymer powder and a first contrast agent (e.g., iron nanoparticles) both dissolved in an organic solvent is prepared and then transferred to a pre-warmed mold and heated to a high temperature (e.g., by placing in an oven set to ~80° C. for ~2 hours). The excess solvent is then removed, e.g., by applying a vacuum to the mold containing the solution mixture, for example, for an additional 2 hours. The resulting polymeric films containing the first contrast agent (e.g., iron nanoparticles) incorporated therein are then detached from the mold and optionally cut to a desired size (e.g., ~1 cm×~1 cm squares). In some embodiments, the solution comprising polymer powder and the first contrast agent (e.g., iron nanoparticles) subjected to solvent casting can further comprise an additional contrast agent, e.g., but not limited to, potassium iodide and/or barium sulfate.

In some embodiments, the tissue marker can be fabricated with or without a piece of wire placed on top of the casted polymeric film. In one embodiment, a piece of Nitinol wire of an appropriate diameter (e.g., ~0.003" diameter) can be placed on top of the casted polymeric film. Another polymeric film is then placed on top of the optional wire and the first casted polymeric film. In some embodiments, an additional contrast agent, e.g., but not limited to, potassium iodide and/or barium sulfate, can be placed between the two polymeric films. The two polymeric films are then melt-sealed together along the entirety of the film area to optionally entrap the wire within the interior of the film.

In some embodiments, the tissue markers described herein can be fabricated using a film extrusion method, which comprises extruding a mixture comprising polymer and at least one contrast agent to form a film or sheet. For example, polymer pellets or powder (e.g., polyethylene pellets or powder) and solid iron oxide nanoparticle powder can be homogenized, mixed, and then fed into the hopper of a twin-screw extruder. The extrudate can exit through a film dye of a desired thickness. In some embodiments, the extrudate can exit through a film dye of thickness of no more than 0.3 mm. The resulting film/sheet can be cut to desired dimensions, either upon exiting the film dye, or at a later time point prior to use.

In some embodiments, the mixture subjected to extrusion can further comprise an additional contrast agent, e.g., but not limited to, potassium iodide and/or barium sulfate.

Figure 10:
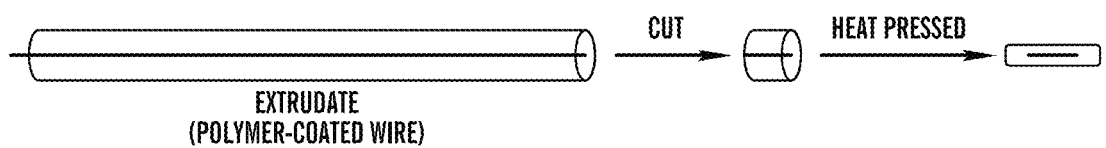
FIG. 10 is a schematic diagram showing processing of an extruded tissue marker from a coaxially-coated wire in accordance with one embodiment described herein.

In some embodiments, the tissue markers described herein can be fabricated using a coaxial wire-coating extrusion method. For example, polymer pellets or powder (e.g., polyethylene pellets or powder) and at least one contrast agent (e.g., iron oxide nanoparticles) can be homogenized, mixed, and then fed into the hopper of a twin-screw extruder. A spool containing a wire to be used as a contrast agent (e.g., a Nitinol wire) can be fed through a crosshead die during extrusion, such that the resulting plastic-coated extrudate wire may contain a polymer matrix-nanoparticle composite coating. The coated wire can then be cut to desired lengths (e.g., approximately 1-cm lengths) and hot-pressed into a flat film, and cut into the desired shape for loading into an introducer needle/cannula. FIG. 10 is a schematic diagram showing a coaxial wire-coating extrusion method to fabricate one or more embodiments of the tissue markers. Alternatively, in some embodiments, the tissue markers described herein can be fabricated, without a wire, using an extrusion method that results in a cylinder that can be cut to desired lengths (e.g., approximately 1-cm lengths) and hot-pressed into a flat film, and cut into the desired shape for loading into an introducer needle/cannula.

In some embodiments, a tissue marker described herein can be manufactured by a process comprising electrospinning. For example, one or more non-biodegradable and/or biodegradable polymers and one or more contrast agents can be mixed with an appropriate solvent to form a solution, suspension, or dispersion, and ejected through a cannula exposed to a high-voltage direct current (HVDC) source, to produce a continuous flexible polymer fiber deposited on a grounded target collector. The fiber mat collected can be cut into an appropriate shape and size.

In various embodiments, the contrast agent(s) can be deposited on the tissue markers described herein. The contrast agent(s) can be deposited on the tissue markers in any desirable pattern. Examples of patterns include, but are not limited to, alphabets, numbers, symbols, or any combinations thereof. In one embodiment, the contrast agent(s) can be deposited on the tissue markers in a pattern comprising at least one alphabet, or at least one numerical digit, or at least one symbol, or any combinations thereof. In one embodiment, the contrast agent(s) can be deposited on the tissue markers in a pattern that can act as an identification tag for the respective tissue markers. Thus, different tissue markers implanted in a tissue can be differentiated accordingly. The contrast agent(s) can be deposited on the tissue markers using any methods known in the art, including, e.g., but not limited to, micropatterning or inkjet printing.

Embodiments of Various Aspects Described Herein can be Defined in any of the Following Numbered Paragraphs 1. A method comprising:
   implanting into tissue at a target tissue site a tissue marker having a flexible polymer matrix arranged in a compact configuration, wherein the flexible polymer matrix has a density and an electrostatic pressure substantially the same as the tissue, and wherein upon the implantation at the tissue target site, the flexible polymer matrix transforms from the compact configuration to an expanded configuration while maintaining the density, and does not migrate for an extended period of time, wherein the target tissue is not an eye tissue.
2. The method of paragraph 1, wherein the tissue is a soft tissue.
3. The method of paragraph 2, wherein the soft tissue is selected from the group consisting of breast tissue, colon tissue, rectal tissue, liver tissue, ovarian tissue, prostate tissue, and lung tissue.
4. The method of paragraph 3, wherein the soft tissue is breast tissue.
5. The method of any of paragraphs 1-4, wherein the tissue marker is implanted without the use of an adhesive.
6. The method of any of paragraphs 1-5, wherein the target tissue site is at, or in close proximity to, the site of a first biopsy.
7. The method of paragraph 6, wherein the target tissue site is at the site of the first biopsy.
8. The method of any of paragraphs 6-7, further comprising, performing a second biopsy at a site different from the target tissue site marked by the tissue marker.
9. The method of paragraph 8, wherein the second biopsy is performed in close proximity to the target tissue site marked by the tissue marker.
10. The method of any of paragraphs 1-9, further comprising implanting at least one additional tissue marker into the tissue.
11. The method of paragraph 10, wherein the additional tissue marker(s) are implanted at another target tissue site(s) from the previous target tissue site(s).
12. The method of paragraph 10 or 11, wherein the additional tissue marker(s) are implanted at the same time or over a period of time.
13. The method of any of paragraphs 1-12, further comprising, determining the location of the implanted tissue marker(s) in the tissue at a first time point.
14. The method of any of paragraphs 1-13, further comprising, determining the location of the implanted tissue marker(s) in the tissue at a second time point, wherein said second time point is subsequent to said first time point.
15. The method of any of paragraphs 1-14, further comprising distinguishing the first tissue marker from the at least one additional tissue marker(s).
16. The method of paragraph 15, wherein the first tissue marker is distinguished from the at least one additional tissue marker by detecting a difference in signal intensities between the first tissue marker and the at least one additional tissue marker under at least one imaging modality.
17. The method of paragraph 16, wherein said at least one imaging modality comprises ultrasound, MRI, x-ray, or any combination thereof
18. The method of paragraph 16 or 17, wherein the first tissue marker and the at least one additional tissue marker comprise different amounts of a MRI-detectable contrast agent (e.g., but not limited to, iron oxide) in the flexible polymer matrix, thereby producing the difference in signal intensities under MRI.
19. The method of any of paragraphs 16-18, wherein the first tissue marker and the at least one additional tissue marker comprise different shapes and/or dimensions of a shape-memory alloy material or an elastic material (e.g., but not limited to, a nitinol wire) in the flexible polymer matrix, thereby producing the difference in signal intensities.
20. The method of paragraph 19, wherein the shape of the shape-memory alloy material or an elastic material (e.g., but not limited to, a nitinol material) is a flat, rectangular ribbon shape, a cylindrical wire, a rectangular bar shape, or any combinations thereof.
21. The method of any of paragraphs 16-20, wherein the first tissue marker and the at least one additional tissue marker comprise different amounts of a radiocontrast agent in the flexible polymer matrix, thereby producing the difference in signal intensities under x-ray.

22. The method of any of paragraphs 16-21, wherein the first tissue marker and the at least one additional tissue marker comprise varying amounts of gas-filled bubbles (including the absence of gas-filled bubbles) in the flexible polymer matrix, thereby producing the difference in signal intensities under ultrasound.

23. The method of any of paragraphs 1-22, further comprising, examining the tissue at, or in close proximity to, the same target tissue site at a second time, wherein said second time point is subsequent to the first time point.

24. The method of any of paragraphs 1-23, further comprising, removing or treating tissue surrounding the same target tissue site at a time point that is after the tissue marker is implanted.

25. The method of any of paragraphs 1-24, wherein the flexible polymer matrix further comprises macropores.

26. The method of paragraph 25, further comprising, growing a plurality of cells into the macropores.

27. A method comprising:
implanting into tissue at a target tissue site a tissue marker having a flexible polymer matrix arranged in a compact configuration, wherein the flexible polymer matrix comprises macropores and has a density substantially the same as the tissue, and wherein upon the implantation at the target tissue site, the flexible polymer matrix transforms from the compact configuration to an expanded configuration while maintaining said density, and
growing a plurality of cells into the macropores, wherein the tissue is not an eye tissue.

28. The method of paragraph 27, wherein the tissue is a soft tissue.

29. The method of paragraph 27 or 28, wherein the soft tissue is selected from a group consisting of breast tissue, colon tissue, rectal tissue, liver tissue, ovarian tissue, prostate tissue, and lung tissue.

30. The method of paragraph 29, wherein the soft tissue is breast tissue.

31. The method of any of paragraphs 27-30, wherein the tissue marker is implanted without the use of an adhesive.

32. The method of any of paragraphs 1-31, wherein the flexible polymer matrix is further adapted to be detectable by at least one imaging modality.

33. The method of any of the preceding paragraphs, wherein the tissue marker does not migrate more than 10 mm from said target tissue site for a period of at least about 1 month.

34. The method of any of the preceding paragraphs, wherein the tissue marker does not migrate more than 10 mm from said target tissue site for a period of at least about 2 years.

35. The method of any of paragraphs 25-34, wherein the macropores form channels between two surfaces of the flexible polymer matrix.

36. The method of paragraph 35, wherein the channels of the macropores have a diameter of about 0.05 mm-2 mm.

37. The method of any of the preceding paragraphs, wherein the tissue marker is implanted into the target tissue site through an injection applicator.

38. The method of any of the preceding paragraphs, wherein the compact configuration is a geometric configuration of the flexible polymer matrix resulted from confinement inside the injection applicator.

39. The method of paragraph 37-38, wherein the injection applicator comprises a needle, a cannula, a catheter, or a combination thereof 40. The method of any of the preceding paragraphs, wherein the flexible polymer matrix in the expanded configuration conforms to a void at the target tissue site, thereby preventing fast migration upon the implantation.

41. The method of any of the preceding paragraphs, wherein the flexible polymer matrix forms a film.

42. The method of any of the preceding paragraphs, wherein the flexible polymer matrix forms a mesh.

43. The method of paragraph 41 or 42, wherein the film or the mesh has a thickness of about 0.05 mm to about 4 mm.

44. The method of any of paragraphs 41-43, wherein the film or the mesh has a dimension of about 0.2 cm to about 1.5 cm.

45. The method of any of paragraphs 32-44, wherein said at least one imaging modality is selected from the group consisting of ultrasound imaging, X-ray-based imaging (including computed tomography), magnetic resonance imaging (MRI), fluorescent imaging, and any combinations thereof 46. The method of any of the preceding paragraphs, wherein the material forming the flexible polymer matrix is detectable by at least a first imaging modality.

47. The method of paragraph 46, wherein the first imaging modality is ultrasound imaging.

48. The method of any of the preceding paragraphs, wherein the flexible polymer matrix is resistant to degradation upon the implantation at the target tissue site.

49. The method of paragraph 48, wherein the material forming the degradation-resistant flexible polymer matrix comprises polyethylene, polypropylene, polytetrafluoroethylene, polyurethanes, polystyrene, polypropylene glycol, or any combinations thereof 50. The method of any of the preceding paragraphs, wherein the flexible polymer matrix is biodegradable.

51. The method of paragraph 50, wherein the material forming the biodegradable flexible polymer matrix comprises polyester, polyamide (e.g., nylon-6, nylon-6,6, nylon-12), polycarbonate, polyhydroxyacids, and any combination thereof.

52. The method of any of the preceding paragraphs, wherein the flexible polymer matrix further comprises at least one contrast agent detectable by said at least one imaging modality.

53. The method of paragraph 52, wherein said at least one contrast agent is detectable by at least magnetic resonance imaging (MRI).

54. The method of paragraph 53, wherein said at least one contrast agent detectable by MRI is selected from the group consisting of metal oxide particles, metal materials, amorphous materials, crystalline materials, and any combinations thereof.

55. The method of any of paragraphs 52-54, wherein said at least one contrast agent is detectable by at least X-ray imaging.

56. The method of paragraph 55, wherein said at least one contrast agent includes a radiopaque material.

57. The method of paragraph 56, wherein the radiopaque material is selected from the group consisting of loxaglate or iodine (HEXABRIX® or CYSTO CON- RAY™II), bromine, salts, metal or alloy materials, metal oxide particles, and any combinations thereof 58. The method of paragraph 54, wherein the metal oxide particles comprise oxide of iron, nitinol (nickel titanium), titanium, tantalum, tungsten, or any combinations thereof 59. The method of paragraph 58, wherein the metal oxide particles comprise iron oxide particles or nanoparticles.

60. The method of paragraph 57, wherein the salts comprise an iodinated salt, barium salts (e.g., barium sulfate), bismuth salts (e.g., bismuth oxychloride), or any combinations thereof.

61. The method of paragraph 57, wherein the metal or alloy materials comprise nitinol (nickel titanium), titanium, tantalum, tungsten, or any combinations thereof.

62. The method of any of paragraphs 52-61, wherein said at least one contrast agent comprises at least two contrast agents forming an integral entity.

63. The method of paragraph 62, wherein the integral entity comprises an iron oxide particle coated with another contrast agent.

64. The method of any of the preceding paragraphs, wherein the flexible polymer matrix further comprises an imaging-signal enhancer.

65. The method of paragraph 64, wherein the imaging-signal enhancer comprises a plurality of gas-filled microbubbles adapted to be detectable by ultrasound imaging.

66. The method of any of the preceding paragraphs, wherein the flexible polymer matrix further comprises an active agent.

67. The method of any of the preceding paragraphs, further comprising contacting the flexible polymer matrix with at least one active agent prior to the implantation.

68. The method of paragraph 66 or 67, wherein the active agent is selected from the group consisting of a therapeutic agent, an anti-cancer agent, an antimicrobial agent, an anesthetic, a cell growth factor, a steroid, a protein, and any combinations thereof 69. The method of paragraph 68, wherein the active agent comprises an antimicrobial agent.

Some Selected Definitions of Terms

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In certain embodiments of the aspects described herein, the subject is a mammal, e.g., a primate, e.g., a human. A subject can be male or female. Preferably, the subject is a mammal. The mammal can be a human, non-human primate, mouse, rat, dog, cat, horse, or cow, but are not limited to these examples. Mammals other than humans can be advantageously used as subjects that represent animal models of tissue repair, regeneration and/or reconstruction. In addition, the methods and compositions described herein can be used to treat domesticated animals and/or pets.

The term "statistically significant" or "significantly" refers to statistical significance and generally means a two standard deviation (2SD) below or above a reference level. The term refers to statistical evidence that there is a difference. It is defined as the probability of making a decision to reject the null hypothesis when the null hypothesis is actually true. The decision is often made using the p-value.

As used herein, the term "substantial" or "substantially" means a proportion of at least about 60%, or preferably at least about 70% or at least about 80%, or at least about 90%, at least about 95%, at least about 97% or at least about 99% or more, or any integer between 70% and 100%. In some embodiments, the term "substantially" means a proportion of at least about 90%, at least about 95%, at least about 98%, at least about 99% or more, or any integer between 90% and 100%. In some embodiments, the term "substantially" can include 100%.

As used herein, the term "comprising" means that other elements can also be present in addition to the defined elements presented. The use of "comprising" indicates inclusion rather than limitation.

The term "consisting of" refers to the components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention Other than in the operating examples, or where otherwise indicated, all numbers expressing quantities of ingredients or reaction conditions used herein should be understood as modified in all instances by the term "about." The term "about" when used in connection with any numeric values may mean±5%.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Unless otherwise explained, all technical and scientific terms used herein have the same meaning as commonly understood by one of ordinary skill in the art to which this disclosure belongs. Definitions of common terms in diseases and disorders, separation and detection techniques can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

All patents and other publications identified throughout the specification are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Some embodiments described herein are further illustrated by the following example which should not be construed as limiting.

The contents of all references cited throughout this application, examples, as well as the figures and tables are incorporated herein by reference in their entirety.

concentration of the contrast agent solutions varied. The solvent (e.g., chloroform) was then allowed to evaporate before encasing the solids within the films, which was performed by melting the film surfaces together.

TABLE 1

Examples of various tissue marker compositions and fabrication methods

| Marker | Matrix | MRI Contrast Agent | X-ray Contrast Agent | Ultrasound Contrast Agent | Method of Manufacture |
|---|---|---|---|---|---|
| A1 | Polyethylene | N/A | Hexabrix ®, 8 mg l | Polyethylene itself | Heat-sealing |
| A2 | Polyethylene | N/A | Hexabrix ®, 4 mg l | Polyethylene itself | Heat-sealing |
| A3 | Polyethylene | N/A | Hexabrix ®, 2 mg l | Polyethylene itself | Heat-sealing |
| A4 | Polyethylene | N/A | Hexabrix ®, 1 mg l | Polyethylene itself | Heat-sealing |
| A5 | Polyethylene | N/A | Hexabrix ®, 0.5 mg l | Polyethylene itself | Heat-sealing |
| A6 | Polyethylene | N/A | Hexabrix ®, 0.25 mg l | Polyethylene itself | Heat-sealing |
| A7 | Polyethylene | N/A | Hexabrix ®, 0.125 mg l | Polyethylene itself | Heat-sealing |
| A8 | Polyethylene | N/A | Hexabrix ®, 0.0625 mg l | Polyethylene itself | Heat-sealing |
| B1 | Polyethylene | Iron Oxide Nanoparticles, 0.125 mg | N/A | Polyethylene itself | Heat-sealing |
| B2 | Polyethylene | Iron Oxide Nanoparticles, 0.0625 mg | N/A | Polyethylene itself | Heat-sealing |
| B3 | Polyethylene | Iron Oxide Nanoparticles, 0.03125 mg | N/A | Polyethylene itself | Heat-sealing |
| B4 | Polyethylene | Iron Oxide Nanoparticles, 0.015625 mg | N/A | Polyethylene itself | Heat-sealing |
| B5 | Polyethylene | Iron Oxide Nanoparticles, 0.0078125 mg | N/A | Polyethylene itself | Heat-sealing |
| B6 | Polyethylene | Iron Oxide Nanoparticles, 0.00390625 mg | N/A | Polyethylene itself | Heat-sealing |
| B7 | Polyethylene | Iron Oxide Nanoparticles, 0.001953125 mg | N/A | Polyethylene itself | Heat-sealing |
| B8 | Polyethylene | Iron Oxide Nanoparticles, 0.0009765625 mg | N/A | Polyethylene itself | Heat-sealing |
| C1 | Polyethylene | N/A | Potassium Iodide, 8 mg l | Polyethylene itself | Heat-sealing |
| C2 | Polyethylene | N/A | Potassium Iodide, 4 mg l | Polyethylene itself | Heat-sealing |
| C3 | Polyethylene | N/A | Potassium Iodide, 2 mg l | Polyethylene itself | Heat-sealing |
| C4 | Polyethylene | N/A | Potassium Iodide, 1 mg l | Polyethylene itself | Heat-sealing |
| C5 | Polyethylene | N/A | Potassium Iodide, 0.5 mg l | Polyethylene itself | Heat-sealing |
| C6 | Polyethylene | N/A | Potassium Iodide, 0.25 mg l | Polyethylene itself | Heat-sealing |
| C7 | Polyethylene | N/A | Potassium Iodide, 0.125 mg l | Polyethylene itself | Heat-sealing |
| C8 | Polyethylene | N/A | Potassium Iodide, 0.0625 mg l | Polyethylene itself | Heat-sealing |
| D | Polyethylene | Iron Oxide Nanoparticles, 0.125 mg | Hexabrix ®, 8 mg l | Polyethylene itself | Heat-sealing |
| E | Polyethylene | Iron Oxide Nanoparticles, 0.125 mg | Titanium Wire | Polyethylene itself | Heat-sealing |
| F | Polyethylene | Nitinol Wire | Nitinol Wire | Polyethylene itself | Heat-sealing |
| G | Polyethylene | Iron Oxide Nanoparticles, 0.125 mg | Nitinol Wire | Polyethylene itself | Heat-sealing |
| H | Polyethylene | Nitinol Wire | Nitinol Wire | Polyethylene itself | Heat-sealing |

EXAMPLES

Example 1. Exemplary Tissue Markers, Fabrication Methods and Visibility of the Tissue Markers Under Different Imaging Modalities Tissue markers A1-H (as shown in Table 1), of an area of about 1 cm², were created by entrapping or dispersing varying amounts of an MRI contrast agent, e.g., but not limited to, superparamagnetic iron oxide nanoparticles, metal wires, or a combination thereof, and/or a X-ray contrast agent, e.g., HEXABRIX®, potassium iodide crystals, metal wires, or any combinations thereof, between two plastic films comprising low density polyethylene (LDPE). The contrast agents were introduced into the plastic films by dispensing solutions of contrast agents onto one or both of the films. The volume of the contrast agent solutions added to the films was constant, e.g., ~25 microliters, while the concentration of the contrast agent solutions varied. The solvent (e.g., chloroform) was then allowed to evaporate before encasing the solids within the films, which was performed by melting the film surfaces together.

The tissue markers were then analyzed under appropriate imaging modalities, e.g., mammography, ultrasound, and/or magnetic resonance imaging. Mammograms were acquired on a Hologic Selenia system with breast compression, ultrasound was performed using a Philips IV22 system with a 17.5 MHz linear array transducer, and MRI imaging was performed on a Philips 1.5 T XR system with a 16 ch head coil.

Figure 2A:
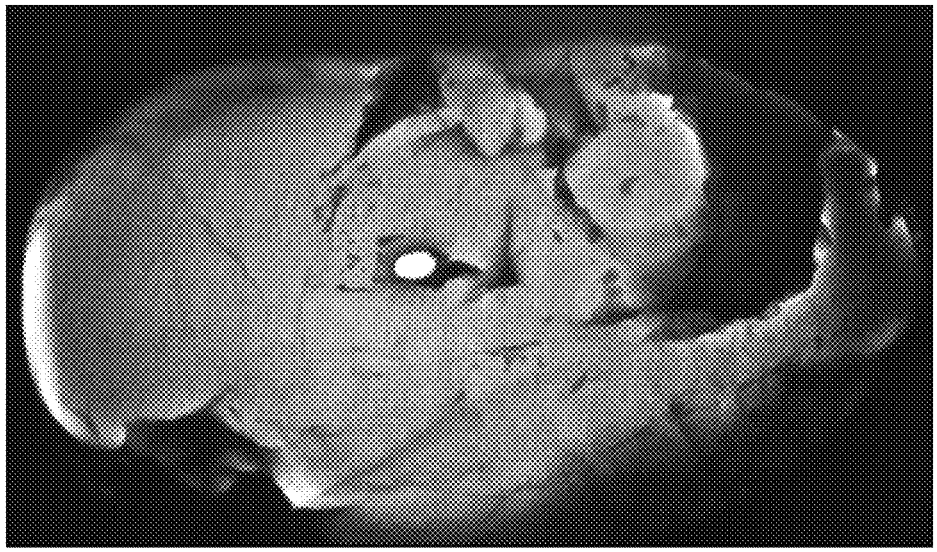
FIGS. 2A-2D are mammograms of a chicken breast injected with one various embodiments of a tissue marker described herein.
Figure 2B:
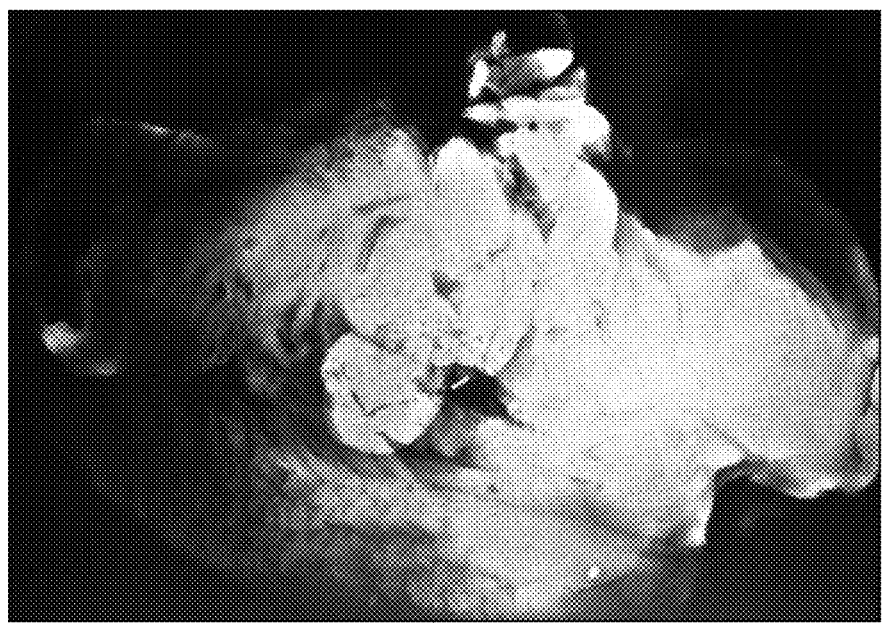
Figure 2C:
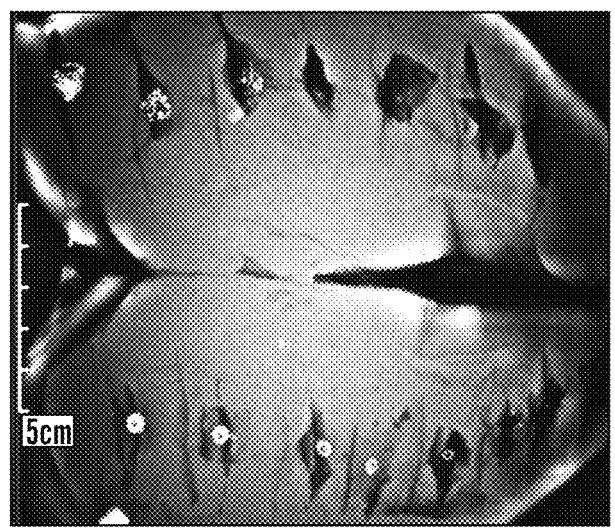

FIGS. 2A-2D show examples of tissue markers described herein that were placed in a chicken breast and visualized by mammography. As shown in FIG. 2A, the bright spot is a signal produced by HEXABRIX® as a radiocontrast agent used in a tissue marker. FIG. 2B is a mammogram of a chicken breast injected with a tissue marker containing a titanium wire as a radiocontrast agent, as depicted by a bright rod shape. FIG. 2C is a mammogram of a chicken breast injected with tissue markers either containing HEXABRIX® (top portion of the image) or potassium iodide (bottom portion of the image), as a radiocontrast agent. From left to right, the amount of iodine in both image portions decreases two-fold each time.

To fabricate tissue markers comprising potassium iodide, e.g., as shown in FIG. 2C, in one embodiment, polyethylene pellets or powder, potassium iodide, and optionally solid iron oxide nanoparticle powder can be homogenized, mixed, and then fed into the hopper of a twin-screw extruder. The extrudate can exit through a film dye, e.g., of thickness not more than 0.3 mm. The resulting film/sheet can be cut to desired dimensions, either upon exiting the film dye, or at a later time point prior to use. In lieu of extrusion, the tissue markers containing polyethylene, potassium iodide, and optionally solid iron oxide nanoparticles can be prepared using the solvent cast and melt sealing approach as described in the following Example 4. The tissue markers can be further prepared using the melt processing approach as described in the following Example 3.

Figure 2D:

FIG. 2D is a mammogram of a chicken breast injected with such the tissue markers containing various nitinol wire lengths (top to bottom: no wire, ~0.25 cm, ~0.5 cm, ~0.75 cm, ~1.0 cm, ~1.25 cm, ~1.5 cm of nitinol wire). Bright lines or rod shapes shown in the mammogram are the signals produced by the nitinol wires dispersed between plastic films (e.g., polyethylene films). To produce the tissue markers shown in FIG. 2D, in some embodiments, organo-soluble (oleic acid-coated) iron oxide nanoparticles (~10 milligrams, mg), ~20-nanometers in diameter, were dispersed in about one milliliter (mL) chloroform. Serial dilutions were performed to provide a range of iron oxide nanoparticle concentrations (e.g., ~10 mg/mL, ~5 mg/mL, ~2.5 mg/mL, ~1.25 mg/mL, ~0.625 mg/mL, and blank film of 0 mg/mL). About fifty microliters (~50 μL) of the resulting nanoparticle dispersion was added onto the surface (e.g., center) of each individual film containing nitinol wires of varying lengths (e.g., ~0.5 cm, ~0.75 cm, ~1.0 cm, ~1.25 cm, and ~1.5 cm) and the chloroform allowed to evaporate to dryness.

Figure 3:
FIG. 3 is an ultrasonography image of a chicken breast injected with a tissue marker comprising a plastic film that can reflect ultrasound waves differently than the breast tissue, which in turn produces a change in signal intensity, as indicated by a bright double-edged line.

FIG. 3 show an example of a tissue marker described herein that was placed in a chicken breast and visualized by ultrasonography. The bright double-edged lines were signals produced by the material of the plastic films (e.g., polyethylene films) itself acting to reflect ultrasound waves differently than the breast tissue.

Figure 4A:
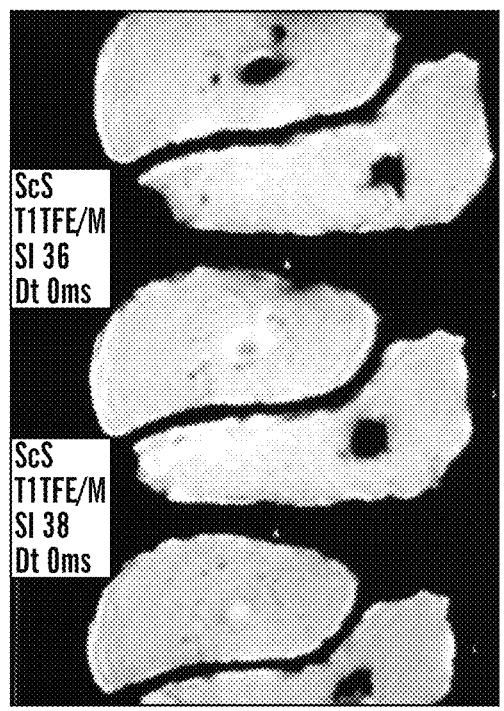
FIGS. 4A-4C are magnetic resonance images of a chicken breast or an agar gel phantom injected with various embodiments of a tissue marker described herein.
Figure 4B:
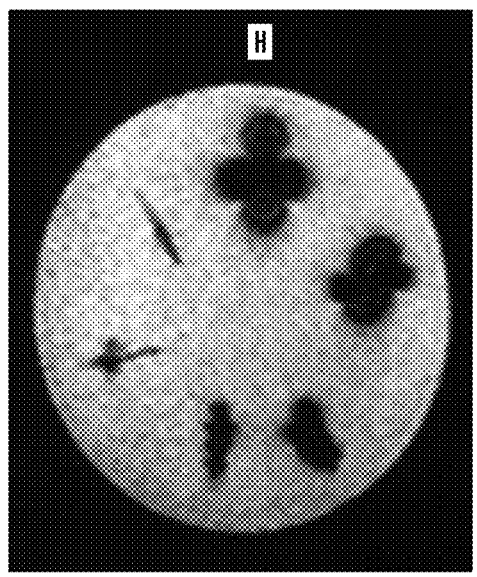
Figure 4C:
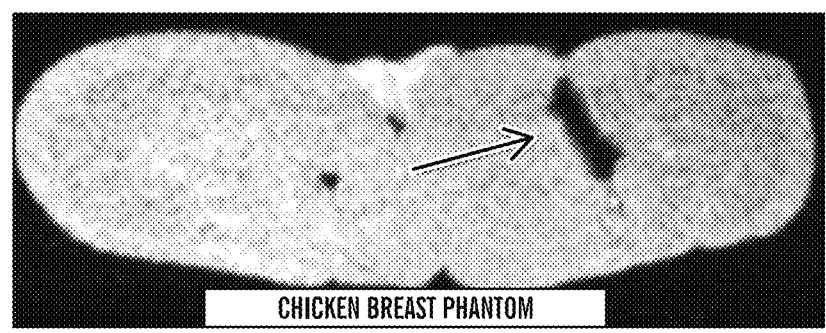

FIGS. 4A-4C show examples of tissue markers described herein that were placed in a chicken breast or a 1% agar gel phantom and visualized by magnetic resonance imaging. As shown in FIG. 4A, the decrease in the signal intensity is produced by a difference in magnetic susceptibility of the superparamagnetic iron oxide nanoparticles and the plastic film (e.g., polyethylene films) as compared to the surrounding tissue. A nitinol wire, in addition to, or in place of, iron oxide nanoparticles can also decrease the signal intensity.

In one embodiment, to produce tissue markers as shown in FIG. 4B, organo-soluble (oleic acid-coated) iron oxide nanoparticles (~10 milligrams, mg), ~20-nanometers in diameter, were dispersed in about one milliliter (mL) chloroform. Serial dilutions were performed to provide a range of concentrations (e.g., ~10 mg/mL, ~5 mg/mL, ~2.5 mg/mL, ~1.25 mg/mL, 0.625 mg/mL, and blank film of 0 mg/mL). About fifty microliters (~50 μL) of the resulting nanoparticle dispersion was dispensed onto the surface (e.g., center) of each individual film and the chloroform allowed to evaporate to dryness. A about one-centimeter nitinol wire (~0.007 inch diameter) was placed on top of the iron oxide nanoparticles, which were then mixed into the film by melting the films together, e.g., with a heat gun. The resulting films were placed into a about one percent by weight (1 wt %) agar gel phantom and imaged under a 1.5-Tesla MRI (FIG. 4B). FIG. 4B is a magnetic resonance image of 1% agar gel phantom loaded with tissue markers containing various iron oxide nanoparticles (top center (H) through clockwise orientation: ~0.5 mg, ~0.25 mg, 0.125 mg, 0.0625 mg, ~0.01 mg and 0 mg particles), indicating that the iron oxide nanoparticles can produce a negative contrast in a T2-weighted MR image and size of the tissue markers are tunable, e.g., depending on the amount of iron oxide nanoparticles dispersed in a plastic film, e.g., a polyethylene film. FIG. 4C is another example of a magnetic resonance image of a chicken breast phantom injected with a tissue marker comprising superparamagnetic iron oxide particles.

As shown earlier in FIG. 2B, a tissue marker comprising an iodine-based salt, e.g., potassium iodide, as a radiocontrast agent was visualized under mammography. The bright spot is the signal produced by the iodine-based salt, e.g., potassium iodide, indicating that, in one embodiment, the tissue markers comprising a plastic film, iodine, and superparamagnetic iron oxide nanoparticles can be readily visualized by MRI, mammogram, and ultrasound imaging modalities.

In some embodiments, a metal wire of a reasonable size and length (e.g., a nitinol wire of ~0.007" diameter was cut to a length of 1 centimeter) was entrapped (e.g., by heat-sealing) within two sheets of plastic films (e.g., polyethylene) so as to produce a signal on both MRI and mammography, and/or to aid in a shape-memory feature for the film upon implantation through a needle or cannula.

Figure 6A:
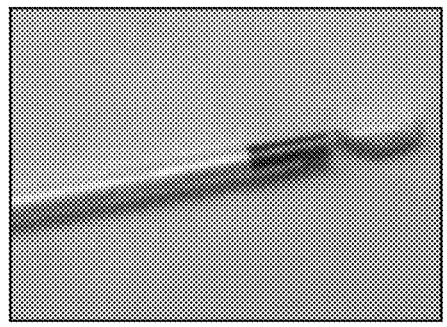
FIGS. 6A-6C is a set of images showing implantation of a tissue marker described herein by ejecting it though a needle. An example tissue marker is rolled up, and inserted into the distal end of an introducer cannula.
Figure 6B:
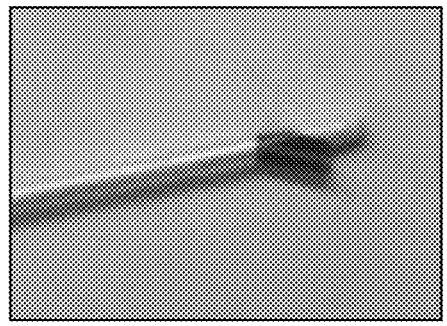
Figure 6C:
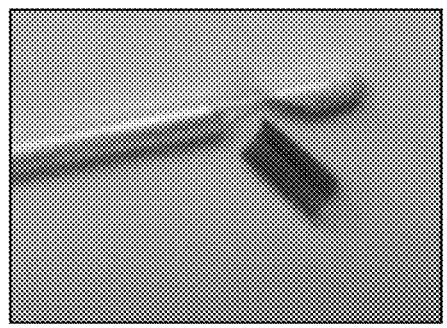

Example 2. Fast Migration Studies of and Response of Cells to Tissue Markers Described Herein Upon Implantation In some embodiments, the tissue markers described herein are confined in a configuration during implantation, e.g., in a needle or a cannula, and then deployed at a target site by ejecting it through the needle or cannula such that the tissue markers transform from a compact configuration (e.g., roll-up) to an expanded configuration, e.g., to conform to a void at the target site (e.g., by unraveling or unrolling the plastic film). For example, as shown in FIGS. 6A-6C, an example tissue marker is rolled up, and inserted into the distal end of an introducer cannula. Upon release from the introducer cannula, the tissue marker starts unrolling to occupy a larger space/volume. In this embodiment, the term "unrolling" is defined herein as a change from a cylindrical shape, as existing in confinement within the introducer, to a larger-diameter shape or a shape that takes up a tissue void space after being released from confinement in the introducer.

Figure 7:
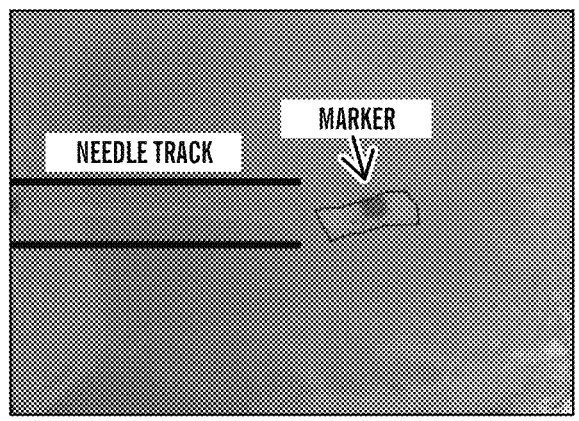
FIG. 7 is an image showing that fast migration of a tissue marker placed in a 1% agar gel phantom did not occur after needle withdrawal. For example, the tissue marker remained at the target site without being pulled back into the needle.

In order to evaluate whether the tissue markers described herein would be pulled back into a needle, an exemplary tissue marker described herein is ejected into ~1% agar gel phantom through a needle. As shown in FIG. 7, the tissue marker stayed at the target site upon implantation, without being pulled back into the needle. Therefore, tissue markers described herein can prevent fast migration (e.g., a tissue marker being drawn or pulled back into a delivery needle or cannula after needle withdrawal).

Figure 8:
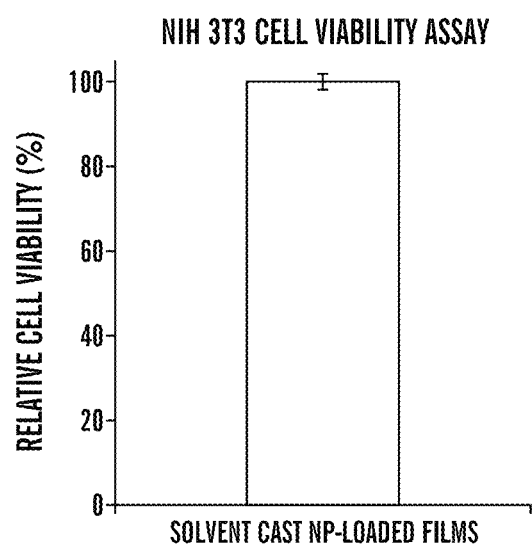
FIG. 8 is a bar graph showing viability of cells after at least 24-hour exposure to one embodiment of a tissue marker described herein for assessment of toxic leachable from the tissue marker.

Tissue markers described herein for use in a subject need to be biocompatible, e.g., minimal or no toxic leachable from the tissue markers that would cause any adverse effect to a subject. In order to assess for the biocompatibility of the tissue markers described herein, a population of cells were seeded in a cell culture plate (e.g., NIH/3T3 seeded at a density of about $4 \times 10^4$ cells/well in a 12-well transwell plate), and exposed to the tissue markers described herein, e.g., tissue markers comprising iron oxide nanoparticles, for a period of time, e.g., at least about 24 hours. The cell viability was then determined by any assay known in the art, e.g., MTS colorimetric assay. As shown in FIG. 8, the tissue markers comprising iron oxide nanoparticles described herein are non-toxic to cells, e.g., mouse fibroblast cells, after at least 24-hour exposure.

Example 3. An Exemplary Method of Fabricating an Example Tissue Marker

In some embodiments, the tissue markers described herein can be fabricated using a melt-processing sealing method, which comprises melting and sealing two polymeric films with iron oxide particles and optionally a wire sandwiched between the two polymeric films. For example, on the top of a pre-formed polymeric film (e.g., a polyethylene film) was added iron oxide nanoparticles dissolved in an organic solvent (e.g., chloroform). The amount of iron oxide nanoparticles added to the polymeric film can vary with the size of polymeric film. In one embodiment, about 50 microliters of iron oxide nanoparticles dissolved in chloroform was added on the top surface of the polymeric film (e.g., a polyethylene film). The solvent was then allowed to evaporate, leaving the iron oxide particles behind. In some embodiments, a solution comprising an additional contrast agent, e.g., but not limited to, potassium iodide and/or barium sulfate, can be added on the top surface of the polymeric film, and excess solvent was then removed to leave the additional contrast agent behind. The tissue marker was then sealed with or without a piece of wire by placing it on the top surface of the polymeric film with the nanoparticles residues disposed thereon. In one embodiment, the wire was a short (e.g., ~0.75 cm) piece of Nitinol wire of an appropriate diameter (e.g., ~0.003" diameter). As shown in FIG. 9A, the Nitinol wire was placed at or around the center of the polyethylene film having nanoparticle residue disposed thereon. A second polymeric film of the same or different material (e.g., a polyethylene film) was subsequently added on top of the nanoparticle residue, and the two films were then sealed together by applying heat and pressure to melt the two films together along the entirety of their shared contact area. A schematic diagram showing a melt processing sealing method to fabricate one or more embodiments of the tissue markers is shown in FIG. 5A.

Example 4. Another Exemplary Method of Fabricating an Example Tissue Marker

In some embodiments, the tissue markers described herein can be fabricated using a solvent casting and melt sealing method, which comprises solvent casting a first polymeric film comprising iron nanoparticles distributed therein, and optionally entrapping a wire between the first polymeric film and a second polymer film using a melt-sealing method. For example, a solution mixture of polymer powder and iron nanoparticles both dissolved in an organic solvent was prepared. In one embodiment, the solution of polymer powder and iron nanoparticles was prepared as follows: polyethylene powder (~750 mg) was dissolved in ~4 mL toluene at ~80° C., and a solution of iron oxide nanoparticles (5 mg), also dissolved in toluene (~1 mL), was subsequently added to the polymer solution and thoroughly mixed. The solution mixture was then transferred to a pre-warmed glass dish and heated to a high temperature (e.g., by placing in an oven set to ~80° C. for ~2 hours). The excess solvent was then removed, e.g., by applying a vacuum to the dish containing the solution mixture, for example, for an additional 2 hours. The resulting polymeric films containing iron nanoparticles therein were then peeled from the bottom of the dish and cut to a desired size (e.g., ~1 cm×~1 cm squares). In some embodiments, the solution comprising polymer powder and iron nanoparticles subjected to solvent casting can further comprise an additional contrast agent, e.g., but not limited to, potassium iodide and/or barium sulfate.

The tissue marker was then fabricated with or without a piece of wire placed on top of a square film. In one embodiment, about 0.75 cm long piece of Nitinol wire of an appropriate diameter (e.g., ~0.003" diameter) was placed on top of one square film. Another polymeric film was placed on top of the wire and the first resultant polymeric square film. In some embodiments, an additional contrast agent, e.g., but not limited to, potassium iodide and/or barium sulfate, can be placed between the two polymeric films. The two polymeric films were melt-sealed together along the entirety of the film area to entrap the wire within the interior of the film. A schematic diagram showing a solvent casting and melt sealing method to fabricate one or more embodiments of the tissue markers is shown in FIG. 5B.

Example 5. Another Exemplary Method of Fabricating an Example Tissue Marker

In some embodiments, the tissue markers described herein can be fabricated using a film or cylindrical extrusion method, which comprises extruding a mixture comprising polymer and iron oxide nanoparticles powder through a profile to form a film, cylinder, or sheet. For example, polymer pellets or powder (e.g., polyethylene pellets or powder) and solid iron oxide nanoparticle powder can be homogenized, mixed, and then fed into the hopper of a twin-screw extruder. The extrudate can exit through a film dye of a desired thickness. In some embodiments, the extrudate can exit through a film dye of thickness not more than 0.3 mm. The resulting film/sheet can be cut to desired dimensions, either upon exiting the film dye, or at a later time point prior to use.

In some embodiments, the mixture subjected to extrusion can further comprise an additional contrast agent, e.g., but not limited to, potassium iodide and/or barium sulfate.

Example 6. Another Exemplary Method of Fabricating an Example Tissue Marker

In some embodiments, the tissue markers described herein can be fabricated using a coaxial wire-coating extrusion method. For example, polymer pellets or powder (e.g., polyethylene pellets or powder) and solid iron oxide nanoparticle powder can be homogenized, mixed, and then fed into the hopper of a twin-screw extruder. A spool containing a wire to be used as a contrast agent (e.g., a Nitinol wire) can be fed through a crosshead die during extrusion, such that the resulting plastic-coated extrudate wire may contain a polymer matrix-nanoparticle composite coating. The coated wire can then be cut to desired lengths (e.g., approximately 1-cm lengths) and hot-pressed into a flat film, and cut into the desired shape for loading into an introducer needle/cannula. FIG. 10 is a schematic diagram showing a coaxial wire-coating extrusion method to fabricate one or more embodiments of the tissue markers.

Figure 11A:
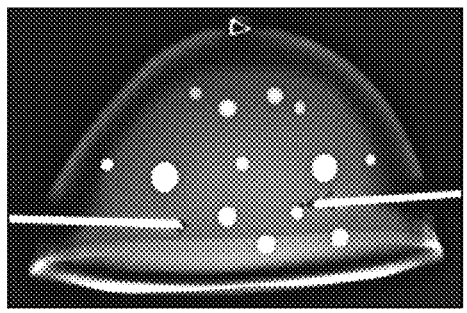
FIGS. 11A-11D is a set of mammogram images showing deployment of one embodiment of the tissue markers described herein in a biopsy training phantom, as visualized under mammography.
Figure 11B:
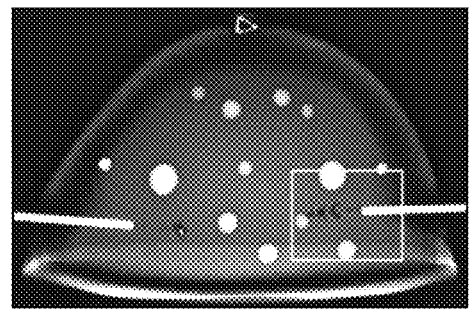
Figure 11C:
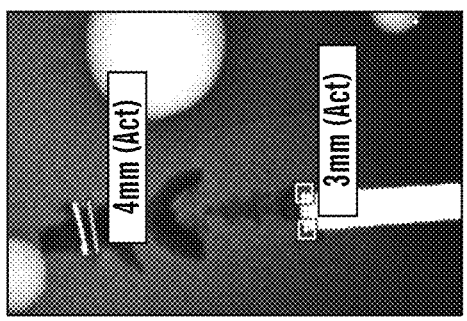
Figure 11D:
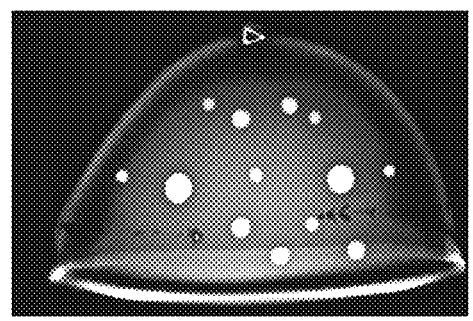

Example 7. Deployment, Unrolling and Visualization of an Example Tissue Marker in a Breast Phantom In this Example, a tissue marker comprising iron nanoparticles and a Nitinol wire entrapped in a polyethylene matrix was rolled up, and loaded into an introducer needle. The introducer needle was placed in a stereotactic breast biopsy training phantom and the tissue marker was partially deployed. A mammogram was then acquired (FIG. 11A). The tissue marker was then fully deployed, and another mammogram was taken (FIG. 11B). The introducer needle was then withdrawn from the phantom, and a third mammogram was acquired. The dimensions of the Nitinol wire and introducer needle, both of which can be seen under mammography were measured and compared. The tissue marker with the Nitinol wire was shown to be larger than the needle track after deployment (FIG. 11C). The tissue marker remained at the deployment site after removing the introducer needle (FIG. 11D).

Figure 12:
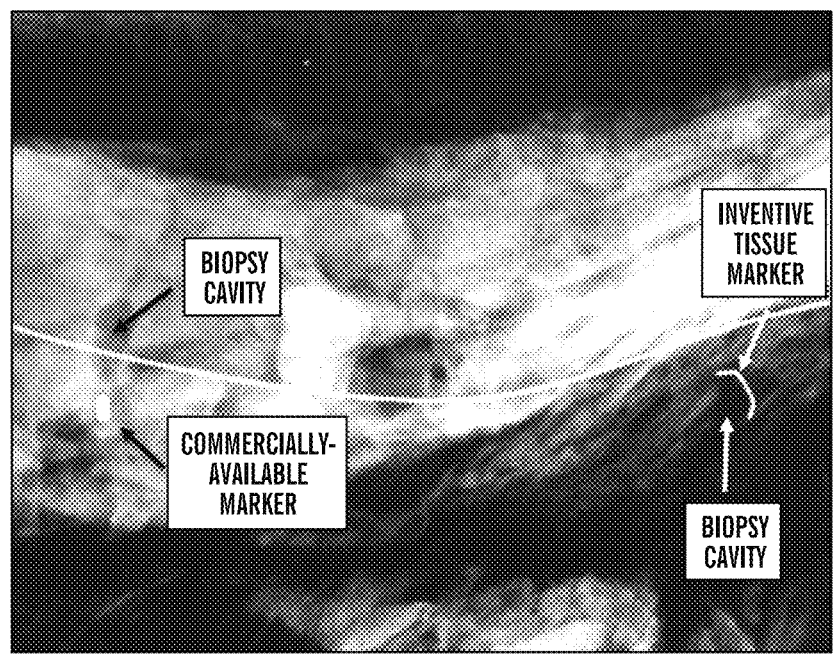
FIG. 12 is a mammogram image of one embodiment of the tissue markers described herein as seen under mammography. The mammogram shows an unrolled tissue marker with the wire (right) after release of compression after a stereotactic core biopsy. The inventive tissue marker did not migrate away from the implantation site. However, the commercially available biopsy marker (left) migrated at least a short distance away from the biopsy cavity.

Example 8. Deployment of an Example Tissue Marker into a Tissue Phantom where a Stereotactic Biopsy was Performed In this Example, a tissue marker comprising iron nanoparticles and a Nitinol wire entrapped in a polyethylene matrix was loaded into an introducer needle and deployed into a stereotactic breast biopsy training phantom under compression, and imaged immediately after deployment while still under compression, and then after the release of compression (FIG. 12). The tissue marker, as seen under mammography, shows an unrolled tissue marker via the wire after release of compression after stereotactic core biopsy. The tissue marker has not migrated. The experiment was also performed with a commercially available biopsy marker. It has migrated a short distance out of the biopsy cavity.

Example 9. Simulation of Long-Term (Slow) Migration in a Tissue Phantom

Figure 13A:
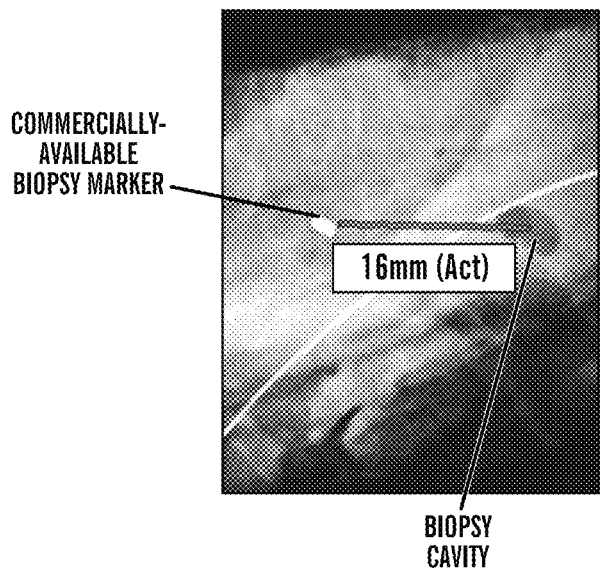
FIGS. 13A-13C are mammogram images and associated quantitative data relating to tissue phantoms containing a commercially available biopsy marker (FIG. 13A) and the tissue marker according to one embodiment described herein (FIG. 13B), respectively, after the tissue phantoms containing the markers were centrifuged at about 2000 rpm for about 16 hours at room temperature. The distances of the tissue marker or the commercially available biopsy marker from the original placement (biopsy cavity) were then measured. The respective long-term migration distances are shown in FIG. 13C as a form of a bar graph.
Figure 13B:
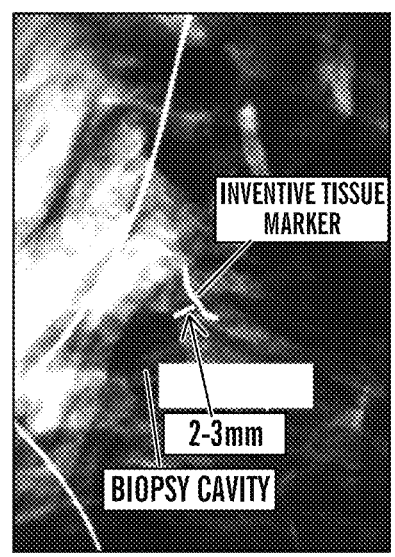
Figure 13C:
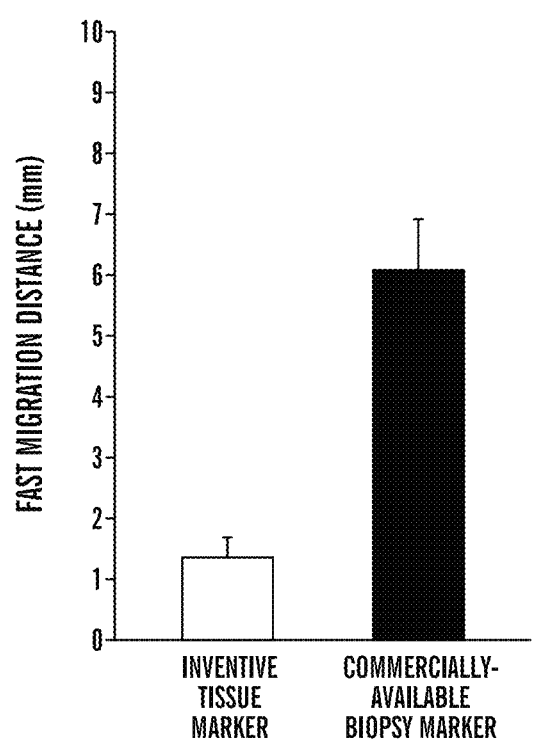

A vacuum-assisted, stereotactic core biopsy of a breast tissue phantom was performed, and an example tissue marker was deployed into the biopsy cavity. A commercially available biopsy marker was also used for comparison. The phantom was then imaged under mammography to assess the placement of the tissue marker. Long-term, or slow, migration was assessed by accelerating the process using centrifugation of the tissue phantom with the tissue marker deployed therein at about 2000 RPM for about 16 hours at room temperature. The phantom was then re-imaged under mammography in multiple orientations and planes, and the distances of the tissue marker relative to the biopsy cavities were measured. The tissue marker in accordance with one embodiment described herein migrated a shorter distance as compared to the migration distance of the commercially available biopsy marker. As shown in FIGS. 13A-13C, the tissue marker according to one embodiment described herein migrated a distance of 2-3 mm as compared to the migration distance of commercially available biopsy marker being about 16 mm.

Example 10. Tuning Artifact Volume of an Example Tissue Marker on MRI

A series of tissue markers according to various embodiments described herein were fabricated. Specifically, tissue markers each comprising a varying amount of iron nanoparticles and a Nitinol wire entrapped in a polyethylene matrix were placed vertically about 2 mm beneath the surface of a 1% agar gel phantom. The tissue markers were spaced about 2 cm apart in the 1% agar gel phantom. The phantoms were then imaged under MRI using different methods (e.g., BiLaterial Imaging in Sagittal view with Sense (BLISS); and Turbo Spin Echo (TSE)) to determine size artifacts (FIG. 14A). The size of the artifact was calculated as an area using Analyze image processing software, and multiplied by the slice thickness (e.g., about 1.5 mm in this Example) in order to determine the artifact volume. The artifact volume was then plotted as a function of iron oxide content to determine the dependence of artifact size (visibility) on iron oxide content (FIG. 14B). FIG. 14B shows that the artifact size of the tissue markers increases with the amount of iron oxide contained in each tissue marker.

Example 11. In Vivo Studies of Exemplary Tissue Markers Deployed in Tissue Voids In this Example, small holes (e.g., of about 1 mm in diameter) were created in the one or more embodiments of the tissue markers described herein to allow anchor of the tissue markers upon implantation in a tissue as the tissue grows in and around the implanted tissue markers.

Figure 15A:
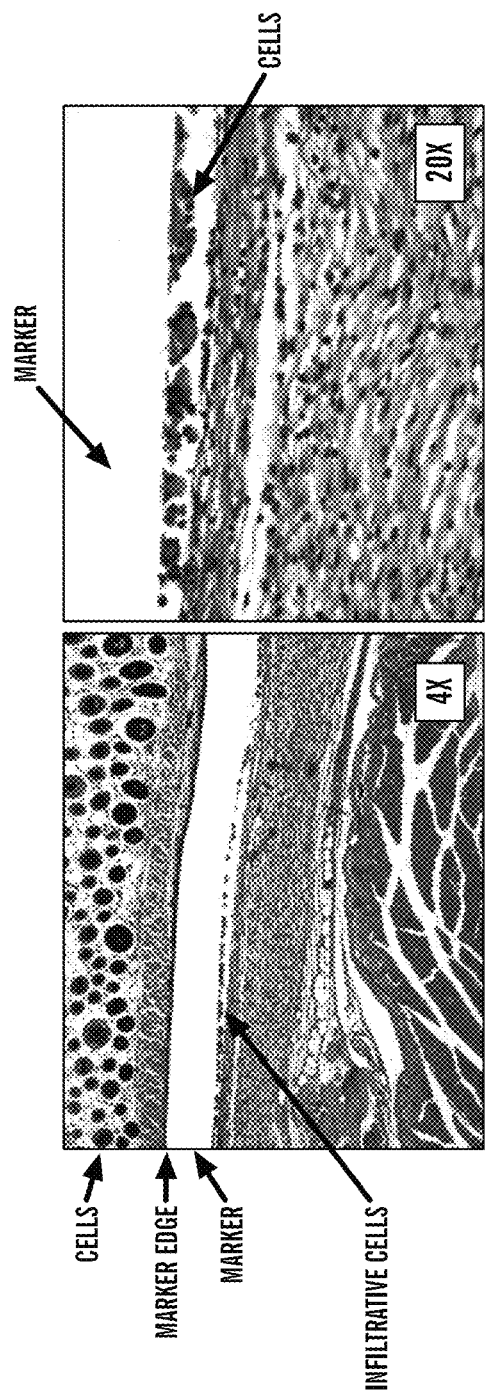
FIGS. 15A-15B are histological micrographs of tissue growth around an exemplary tissue marker described herein after 1 week and 4 weeks of implantation, respectively.
Figure 15B:
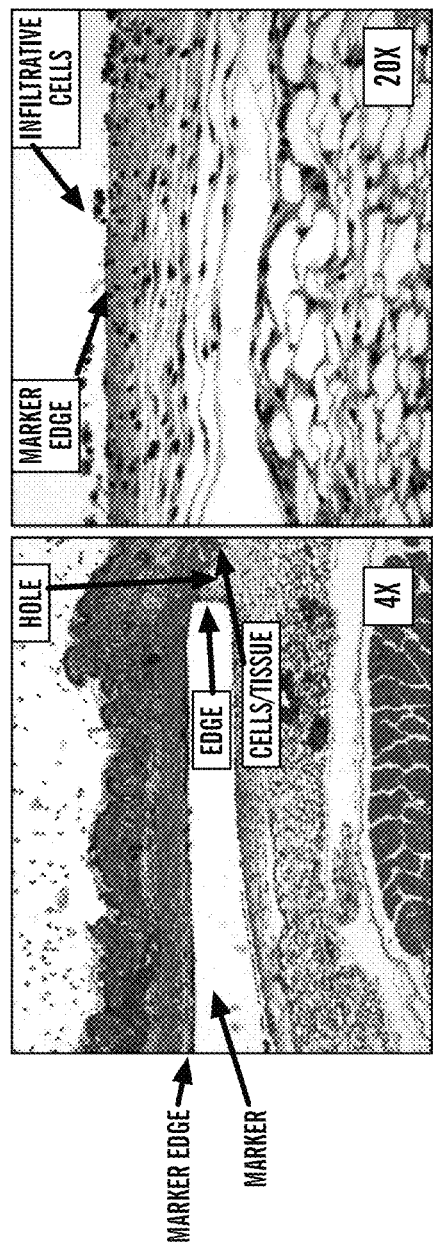

For in vitro studies, an incision was made in the back of a wild type B6 mouse and an example tissue marker with small holes was implanted therein. At about 1 week and 4 weeks the animals were sacrificed and the implanted tissue marker was removed and analyzed. Histological analysis of 1-week (FIG. 15A) and 4-week (FIG. 15B) samples shows that the tissue had grown around the tissue markers and the tissue markers were integrated well into the tissue, as evident by the presence of cells/nuclei (dark circles) and deposition of extracellular matrix. The tissue marker materials do not elicit unfavorable biological response and the tissue is able to grow around the implanted tissue markers at either the edges or holes.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:
1. An injection applicator for implanting an implantable tissue marker into a target site, the injection applicator comprising:
    a cannula defining a lumen with an open end; and
    the implantable tissue marker located within the lumen and comprising:
        a sheet having opposing first and second surfaces and comprising at least a first layer of flexible polymer matrix and a second layer of flexible polymer matrix, wherein the sheet is expandable from a rolled configuration to at least a partially unrolled configuration; and
        a shape-memory element located between the first and second surfaces;
        wherein the shape-memory element comprises a shape-memory alloy material that is configured for movement between a compact configuration to an expanded configuration; and
        wherein at least one of the sheet and the shape-memory element is visible by a first imaging modality.

2. The injection applicator of claim 1, wherein the shape-memory element comprises at least one wire, wherein the wire is made of a nickel-titanium alloy.

3. The injection applicator of claim 2, wherein at least one of the first and second layers is a film.

4. The injection applicator of claim 3, wherein the film is a low density polyethylene film.

5. The injection applicator of claim 1, wherein the sheet comprises nanoparticles.

6. The injection applicator of claim 5, wherein the nanoparticles are iron oxide.

7. The injection applicator of claim 1, wherein the sheet is visible by the first imaging modality and the shape-memory element is visible by a second imaging modality, which is different than the first imaging modality.

8. The injection applicator of claim 1, wherein at least one of the first and second layers is elastic.

9. An injection applicator for implanting an implantable tissue marker into a target site, the injection applicator comprising:
a cannula defining a lumen with an open end; and
the implantable tissue marker located within the lumen and comprising:
a sheet expandable from a compact configuration to an expanded configuration, which has at least one dimension greater than the compact configuration; and
a shape-memory element carried within the sheet and expandable with the sheet between the compact configuration and expanded configuration;
wherein the shape-memory element comprises at least one wire comprising a shape-memory alloy material;
wherein at least one of the sheet and the shape-memory element is visible by a first imaging modality; and
wherein the sheet is in a rolled configuration and the shape-memory element is in the compact configuration when the implantable tissue marker is within the lumen, and the shape-memory element moves toward the expanded configuration to move the sheet to a partially unrolled configuration when the implantable tissue marker is deployed from the lumen.

10. The injection applicator of claim 9, wherein the sheet and the shape-memory element are visible by a second imaging modality, which is different from the first imaging modality.

11. The injection applicator of claim 9, wherein the shape-memory element comprises a shape-memory alloy, and the shape-memory alloy comprises:
at least one of a copper-aluminum-nickel alloy or a nickel-titanium alloy; or
at least two or more of zinc, copper, gold, or iron.

12. The injection applicator of claim 9, wherein the sheet comprises at least two layers and the shape-memory element is located between the two layers.

13. The injection applicator of claim 12, wherein the at least two layers are films.

14. The injection applicator of claim 13, wherein the films are made of low density polyethylene.

15. The injection applicator of claim 9, wherein the shape-memory element comprises a viscoelastic element.

16. The implantable tissue marker of claim 9, wherein the sheet comprises nanoparticles that are visible by the first imaging modality.

17. An injection applicator for implanting an implantable tissue marker into a target site, the injection applicator comprising:
a cannula defining a lumen with an open end; and
the implantable tissue marker located within the lumen and comprising:
a biocompatible, elastic sheet having opposite first and second surfaces, wherein the elastic sheet comprises at least a first layer of flexible polymer matrix and a second layer of flexible polymer matrix, which is elastically expandable from a rolled compact configuration to an expanded partially unrolled configuration; and
a shape-memory element located between the first and second surfaces when the elastic sheet is in an unrolled configuration and when in the rolled compact configuration;
wherein the shape-memory element comprises at least one wire comprising a shape-memory alloy material; and
where the expanded partially unrolled configuration has at least one dimension greater than the rolled compact configuration, and wherein the elastic sheet is visible by at least one imaging modality.

18. The injection applicator of claim 17, wherein the elastic sheet has the same density in the rolled compact configuration and the expanded partially unrolled configuration.

19. The injection applicator of claim 17, wherein the elastic sheet has a square shape.

20. The injection applicator of claim 17, wherein the elastic sheet comprises at least one of a membrane, film, mat or mesh.

21. The injection applicator of claim 17, wherein the elastic sheet comprises at least one of a polymer, polymer matrix, woven fibers, or non-woven fibers.

22. The injection applicator of claim 17, wherein the at least one imaging modality comprises at least a first imaging modality and a second imaging modality which is different from the first imaging modality.

23. The injection applicator of claim 17, wherein the at least one imaging modality comprises one of magnetic resonance imaging, mammography, x-ray-based imaging, ultrasound, fluorescence, or computed tomography.

24. The injection applicator of claim 17, wherein the elastic sheet comprises nanoparticles visible by the at least one imaging modality.

25. The injection applicator of claim 17, wherein the elastic sheet comprises at least one of penetrating pores, macropores, air pockets or nanoparticles visible by the at least one imaging modality.

26. The injection applicator of claim 17, wherein the second layer couples to a top surface of the first layer and the shape-memory element is located between the first and second layers.

27. The injection applicator of claim 9, wherein the sheet includes opposing first and second surfaces and wherein the shape-memory element is located between the first surface and the second surface.

28. The injection applicator of claim 1, wherein the density of the flexible polymer matrix is capable of being maintained for a period of at least 60 seconds after implanting into the target site and while expanding from the rolled configuration to the at least a partially unrolled configuration.

29. The injection applicator of claim 9, wherein the density of the sheet is capable of being maintained for a period of at least 60 seconds after implanting into the target site and while expanding from the compact configuration to the expanded configuration.

30. The injection applicator of claim 17, wherein the density of the flexible polymer matrix is capable of being maintained for a period of at least 60 seconds after implanting into the target site and while expanding from the rolled compact configuration to the expanded partially unrolled configuration.

31. The injection applicator of claim 1, wherein the flexible polymer matrix has a density that differs by no more than 30% from a target tissue, which is a soft tissue selected from the group consisting of breast tissue, colon tissue, rectal tissue, liver tissue, ovarian tissue, prostate tissue, and lung tissue.

32. The injection applicator of claim 9, wherein the sheet has a density that differs by no more than 30% from a target tissue, which is a soft tissue selected from the group consisting of breast tissue, colon tissue, rectal tissue, liver tissue, ovarian tissue, prostate tissue, and lung tissue.

33. The injection applicator of claim 17, wherein the flexible polymer matrix has a density that differs by no more than 30% from a target tissue, which is a soft tissue selected from the group consisting of breast tissue, colon tissue, rectal tissue, liver tissue, ovarian tissue, prostate tissue, and lung tissue.

\* \* \* \* \*